US009738853B2

(12) United States Patent
Snead et al.

(10) Patent No.: US 9,738,853 B2
(45) Date of Patent: Aug. 22, 2017

(54) RENEWABLY DERIVED ALDEHYDES AND METHODS OF MAKING AND USING THE SAME

(71) Applicant: Elevance Renewable Sciences, Inc., Woodridge, IL (US)

(72) Inventors: Thomas E. Snead, Woodridge, IL (US); Demond L. Gildon, Woodridge, IL (US); Steven A. Cohen, Woodridge, IL (US); Leslie V. Beltran, Woodridge, IL (US); Robin Weitkamp, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/639,864

(22) Filed: Mar. 5, 2015

(65) Prior Publication Data

US 2015/0252290 A1 Sep. 10, 2015

Related U.S. Application Data

(60) Provisional application No. 61/948,836, filed on Mar. 6, 2014.

(51) Int. Cl.
*C07C 51/10* (2006.01)
*C11B 3/02* (2006.01)
*C11C 3/10* (2006.01)

(52) U.S. Cl.
CPC . *C11B 3/02* (2013.01); *C11C 3/10* (2013.01)

(58) Field of Classification Search
CPC .................................. C11B 3/02; C11C 3/10
USPC ......................................................... 554/128
See application file for complete search history.

(56) References Cited

U.S. PATENT DOCUMENTS 5,756,854 A * 5/1998 Bahrmann ........... B01J 31/0239 568/17
7,615,658 B2 11/2009 Lysenko et al.
8,124,812 B2 2/2012 Lysenko et al.

OTHER PUBLICATIONS

E.N. Frankel et al., 'Catalytic hydroformylation and hydrocarboxylation of unsaturated fatty compounds', 1977, J. Am. Oil Chemists' Soc., vol. 54, pp. 873A-881A.*

(Continued)

*Primary Examiner* — Deborah D Carr
(74) *Attorney, Agent, or Firm* — Kilpatrick Townsend & Stockton LLP

(57) ABSTRACT

Methods for making specialty chemical products and chemical intermediates using hydroformylation are generally disclosed. Further, compositions and compounds formed using such methods are also disclosed. In some embodiments, methods are disclosed for refining a renewably sourced material, such as a natural oil, to form compositions, which can be further reacted employing the methods disclosed herein to form certain specialty chemical products or chemical intermediates.

8 Claims, 1 Drawing Sheet

(56) References Cited

OTHER PUBLICATIONS

D3: Francesca M. Kerton et al., RSC green chemistry series, 'Eco-friendly synthesis of fine chemicals', edited by Roberto Ballini, Cambridge, UK: The royal society of chemistry, 2009, pp. 25-44.*
Int'l Search Report & Written Opinion of the Int'l Search Authority, PCT App. No. PCT/US2015/019002, dated Jun. 16, 2015.
Frankel et al., J. Am. Oil Chemists' Soc., vol. 54, pp. 873A-881A (1977).
Van Rooy et al. J. Organometallic Chem., vol. 507, pp. 69-73 (1996).
Kerton et al., Eco-Friendly Synthesis of Fine Chemicals, Balini, ed., pp. 25-44 (2009).

* cited by examiner

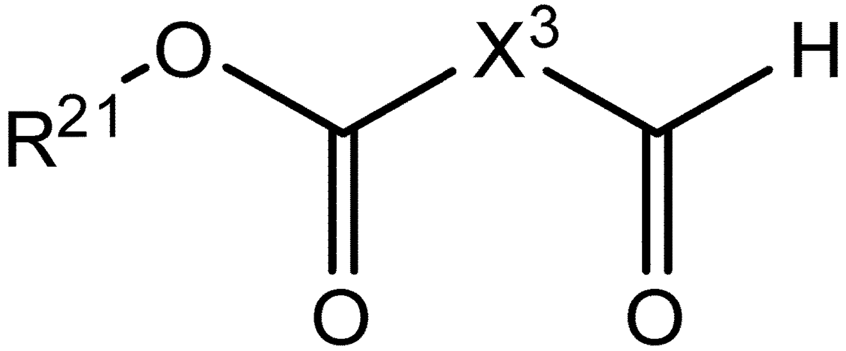

RENEWABLY DERIVED ALDEHYDES AND METHODS OF MAKING AND USING THE SAME

CROSS-REFERENCE TO RELATED APPLICATIONS

The present application claims the benefit of priority of U.S. Provisional Application No. 61/948,836, filed Mar. 6, 2014, which is hereby incorporated by reference as though fully set forth herein in its entirety.

TECHNICAL FIELD

Methods for making specialty chemical products and chemical intermediates using hydroformylation are generally disclosed. Further, compositions and compounds formed using such methods are also disclosed. In some embodiments, methods are disclosed for refining a renewably sourced material, such as a natural oil, to form compositions, which can be further reacted employing the methods disclosed herein to form certain specialty chemical products or chemical intermediates.

BACKGROUND

Natural oils, such as seed oils, and their derivatives can provide useful starting materials for making a variety of chemical compounds. Because such compounds contain a certain degree of inherent functionality that is otherwise absent from petroleum-sourced materials, it can often be more desirable, if not cheaper, to use natural oils or their derivatives as a starting point for making certain compounds. Additionally, natural oils and their derivatives are generally sourced from renewable feedstocks. Thus, by using such starting materials, one can enjoy the concomitant advantage of developing useful chemical products without consuming limited supplies of petroleum. Further, refining natural oils can be less intensive in terms of the severity of the conditions required to carry out the refining process.

Natural oils can be refined in a variety of ways. For example, processes that rely on microorganisms can be used, such as fermentation. Chemical processes can also be used. For example, when the natural oils contain at least one carbon-carbon double bond, olefin metathesis can provide a useful means of refining a natural oil and making useful chemicals from the compounds in the feedstock.

Metathesis is a catalytic reaction that involves the interchange of alkylidene units among compounds containing one or more double bonds (e.g., olefinic compounds) via the cleavage and formation of carbon-carbon double bonds. Metathesis may occur between two like molecules (often referred to as "self-metathesis") and/or it may occur between two different molecules (often referred to as "cross-metathesis"). Self-metathesis may be represented schematically as shown below in Equation (A):

$$R^a—CH═CH—R^b+R^a—CH═CH—R^b \leftrightarrows R^a—CH═CH—R^a+R^b—CH═CH—R^b, \quad (A)$$

wherein $R^a$ and $R^b$ are organic groups.

Cross-metathesis may be represented schematically as shown below in Equation (B):

$$R^a—CH═CH—R^b+R^c—CH═CH—R^d \leftrightarrows R^a—CH═CH—R^c+R^a—CH═CH—R^d+R^b—CH═CH—R^c+R^b—CH═CH—R^d, \quad (B)$$

wherein $R^a$, $R^b$, $R^c$, and $R^d$ are organic groups. Self-metathesis will also generally occur concurrently with cross-metathesis.

In recent years, there has been an increased demand for environmentally friendly techniques for manufacturing materials typically derived from petroleum sources, which can be made by processes that involve olefin metathesis. This has led to studies of the feasibility of manufacturing biofuels, waxes, plastics, and the like, using natural oil feedstocks, such as vegetable and/or seed-based oils. In at least one example, metathesis catalysts can be used to manufacture candle wax, which is described in PCT Publication No. WO 2006/076364, and which is herein incorporated by reference in its entirety. Metathesis reactions involving natural oil feedstocks or compounds derived from them also offer promising solutions for today and for the future.

Natural oil feedstocks of interest include, but are not limited to, oils such as natural oils (e.g., vegetable oils, fish oils, algae oils, and animal fats), and derivatives of natural oils, such as free fatty acids and fatty acid alkyl (e.g., methyl) esters. These natural oil feedstocks may be converted into industrially useful chemicals (e.g., waxes, plastics, cosmetics, biofuels, etc.) by any number of different metathesis reactions. Significant reaction classes include, as non-limiting examples, self-metathesis, cross-metathesis with olefins, and ring-opening metathesis reactions. Non-limiting examples of useful metathesis catalysts are described in further detail below.

Many specialty chemicals and chemical intermediates are derived from refining petroleum products. Such processes generally involve cracking and refining crude petroleum to obtain olefin fragments having a small number of carbon atoms (e.g., two or three carbons). To form longer-chain compounds, the fragments must be reacted to with other such fragments and/or other compounds to form compounds having longer carbon chains. This process is energy-intensive and time-intensive. Further, such processes contributes to the further depletion of non-renewable sources of material. Refining processes for natural oils (e.g., employing metathesis) can lead to compounds having chain lengths closer to those generally desired for chemical intermediates of specialty chemicals (e.g., about 9 to 15 carbon atoms). Thus, refining of natural oils may, in many instances, provide a more chemically efficient and straightforward way to make certain chemical intermediates and specialty chemicals. Further, such processes do not substantially deplete non-renewable sources, such as petroleum. Thus, there is a continuing need to develop processes for making certain chemical intermediates and specialty chemicals using process that employ the refining of natural oils.

SUMMARY

Methods for making certain chemical intermediates and specialty chemicals from a renewable source are disclosed.

In at least one aspect, methods are disclosed for refining certain olefinic ester compounds, comprising: providing a reactant composition comprising olefinic ester compounds; and reacting the olefinic ester compounds with $H_2$ and CO in the presence of a hydroformylation catalyst to form a product composition comprising formylated ester compounds or hydroxylated ester compounds. In some embodiments, the olefinic ester compounds in the reactant composition are derived from a renewable source, such as a natural oil or a derivative thereof. In some such embodiments, the olefinic ester compounds in the reactant composition are derived from a natural oil by a process that includes metathesis.

In another aspect, methods are disclosed for refining certain olefins, comprising: providing a reactant composition comprising olefins; and reacting the olefins with $H_2$ and CO in the presence of a hydroformylation catalyst to form a product composition comprising aldehydes or alcohols. In some embodiments, the olefins in the reactant composition are derived from a renewable source, such as a natural oil or a derivative thereof. In some such embodiments, the olefins in the reactant composition are derived from a natural oil by a process that includes metathesis.

Further aspects and embodiments are disclosed in greater detail in the detailed description, the drawings, and the claims.

BRIEF DESCRIPTION OF DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

The FIGURE shows a non-limiting example of a compound made by the methods of certain embodiments disclosed herein, wherein: $X^3$ is $C_{3-18}$ alkylene, $C_{3-18}$ alkenylene, $C_{2-18}$ heteroalkylene, or $C_{2-18}$ heteroalkenylene, each of which is optionally substituted one or more times; and $R^{21}$ is $C_{1-12}$ alkyl, $C_{1-12}$ heteroalkyl, $C_{2-12}$ alkenyl, or $C_{2-12}$ heteroalkenyl, each of which is optionally substituted one or more times.

DETAILED DESCRIPTION

The following description recites various aspects and embodiments of the inventions disclosed herein. No particular embodiment is intended to define the scope of the invention. Rather, the embodiments merely provide non-limiting examples of various methods, systems, and compositions that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ terms and phrases not expressly defined herein. Such terms and phrases that are not expressly defined shall have the meanings that they would possess within the context of this disclosure to those of ordinary skill in the art to which this disclosure pertains. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion.

As used herein, the term "metathesis catalyst" includes any catalyst or catalyst system that catalyzes an olefin metathesis reaction.

As used herein, the terms "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated triglycerides (as defined below). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, the term "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, the term "unsaturated glyceride" refers to mono-, di-, or tri-esters of glycerol, which include one or more carbon-carbon double bonds. For example, in some embodiments, the "unsaturated glyceride" can be represented by the formula $R—O—CH_2—CH(OR')—CH_2(OR'')$, wherein at least one of R, R', and R'' is a substituted or unsubstituted alkenyl group. In some embodiments, the other group(s) are hydrogen, alkyl, or alkenyl. Examples of unsaturated triglycerides include certain unsaturated fats derived from natural oils.

As used herein, the terms "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin matethesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the terms "hydroformylate" or "hydroformylating" refer to the reacting of a carbon-carbon double bond in the presence of a hydroformylation catalyst to form a hydroformylated product comprising one or more formylated compounds, such as aldehydes. In some embodiments, the reaction occurs in the presence of $H_2$ and CO. The aldehydes in the hydroformylated product need not be isolated. In certain embodiments, the aldehydes can be reacted in the same pot almost immediately after their formation to form other compounds, e.g., hydroformylating an alkene at high $H_2$ partial pressure such that in the same pot the unsaturated compound is converted to a hydroxylated without the intervening isolation of the aldehyde. As used herein, the terms "selective hydroformylation" or "selectively hydroformylating" refer to reacting a species having two or more carbon-carbon double bonds, where only one of the two carbon-carbon double bonds is formylated (e.g., a terminal carbon-carbon double bond in a species is formylated, while an internal carbon-carbon double bond in the same species is not).

Hydroformylation is often carried out in the presence of a catalyst, such as an organometallic complex, which can be referred to as a "hydroformylation catalyst." The product composition of a hydroformylation reaction can contain various metal-containing derivatives of the hydroformylation catalyst, e.g., that are generated via use of the catalyst in a catalytic reaction. These catalyst derivatives can be referred to as "hydroformylation catalyst residues."

As used herein, the term "phase" refers to a region of space within which the physical properties of a material are essentially uniform. For example, solids, liquids, and gases are common descriptions of phases. In some instances, a liquid containing two or more components may separate into two or more separate phases, such as when oil and water are mixed. When two such separate liquid phases are compared, typically one of the two phases is relatively more hydrophilic than the other, referred to as a "polar phase," while the other is relatively more hydrophobic than the other, referred to herein as the "nonpolar phase." For example, when water and oil separate into different phases, the water phase is the polar phase, while the oil phase is the nonpolar phase.

As used herein, the terms "ester" or "esters" refer to compounds having the general formula: R—COO—R', wherein R and R' denote any organic group (such as alkyl, alkenyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths.

As used herein, the term "olefinic ester compounds" refers to a compounds having the general formula: R—COO—R', where R is an optionally substituted alkenyl group and R' is as defined above. In some such embodiments, R is an unsubstituted alkenyl group having from 3 to 18 carbon atoms, and R' is an unsubstituted alkyl group having from 1 to 6 carbon atoms. The compounds can have different carbon lengths for various R and R'. As used herein, the term "terminal olefinic ester compounds" refers to olefinic ester compounds, as defined above, where the alkenyl group, R, includes a terminal carbon-carbon double bond. By contrast, the term "internal olefinic ester compounds" refers to olefinic ester compounds, as defined above, where the alkenyl group, R, does not include a terminal carbon-carbon double bond. Further, as used herein, the term "monounsaturated olefinic ester compounds" refers to olefinic ester compounds, as defined above, where the alkenyl group, R, includes only one carbon-carbon double bond. As used herein, the term "diunsaturated olefinic ester compounds" refers to olefinic ester compounds, as defined above, where the alkenyl group, R, includes exactly two carbon-carbon double bonds. By further analogy, the term "polyunsaturated olefinic ester compounds" refers to olefinic ester compounds, as defined above, where the alkenyl group, R, includes more than one carbon-carbon double bond.

As used herein, the term "formylated ester compound" refers to a compound having the general formula: R—COO—R', where R is an optionally substituted alkyl or alkenyl group that at least contains one formyl (i.e., —CHO) substituent, and R' is as defined above. In some such embodiments, R is an alkyl group having from 3 to 18 carbon atoms and at least one formyl substituent, and R' is an unsubstituted alkyl group having from 1 to 6 carbon atoms. The compounds can have different carbon lengths for various R and R'. Further, as used herein, the term "α,ω-formylated ester compounds" refers to formylated ester compounds, as defined above, where R is an alkyl group having from 3 to 18 carbon atoms and one of the one or more formyl substituents is attached to a —$CH_2$— group, e.g., as part of a —$CH_2$—CHO moiety. Further, as used herein, the term "α,ψ-formylated ester compounds" refers to formylated ester compounds, as defined above, where R is an alkyl group having from 3 to 18 carbon atoms and one of the one or more formyl substituents is attached to a carbon atom that is immediately adjacent to a —$CH_3$ group, e.g., as part of a —CH(—CHO)—$CH_3$ moiety. Also, as used herein, "non-hydroxylated formylated ester compounds" refers to formylated ester compounds, as defined above, where R contains no hydroxyl (—OH) substituents.

As used herein, the term "hydroxylated ester compound" refers to a compound having the general formula: R—COO—R', where R is an optionally substituted alkyl or alkenyl group that at least contains one hydroxyl (—OH) substituent, and R' is as defined above. In some such embodiments, R is an alkyl group having from 3 to 18 carbon atoms and at least one hydroxyl substituent, and R' is an unsubstituted alkyl group having from 1 to 6 carbon atoms. The compounds can have different carbon lengths for various R and R'. Further, as used herein, the term "α,ω-hydroxylated ester compounds" refers to hydroxylated ester compounds, as defined above, where R is an alkyl group having from 3 to 18 carbon atoms and one of the one or more hydroxyl substituents is attached to a —$CH_2$— group, e.g., as part of a —$CH_2$—OH moiety. Further, as used herein, the term "α,ψ-hydroxylated ester compounds" refers to hydroxylated ester compounds, as defined above, where R is an alkyl group having from 3 to 18 carbon atoms and one of the one or more hydroxyl substituents is attached to a carbon atom that is immediately adjacent to a —$CH_3$ group, e.g., as part of a —CH(—OH)—$CH_3$ moiety.

As used herein, the term "aminated ester compound" refers to a compound having the general formula: R—COO—R', where R is an optionally substituted alkyl or alkenyl group that at least contains one amino (—$NR^xR^y$) substituent, R' is as defined above, and $R^x$ and $R^y$ are independently hydrogen or an organic group (e.g., alkyl, alkenyl, or aryl groups). In some such embodiments, R is an alkyl group having from 3 to 18 carbon atoms and at least one amino substituent, and R' is an unsubstituted alkyl group having from 1 to 6 carbon atoms. The compounds can have different carbon lengths for various R and R'. Further, as used herein, the term "α,ω-aminated ester compounds" refers to aminated ester compounds, as defined above, where R is an alkyl group having from 3 to 18 carbon atoms and one of the one or more amino substituents is attached to a —$CH_2$— group, e.g., as part of a —$CH_2$—$NR^xR^y$ moiety. Further, as used herein, the term "α,ψ-aminated ester compounds" refers to aminated ester compounds, as defined above, where R is an alkyl group having from 3 to 18 carbon atoms and one of the one or more amino substituents is attached to a carbon atom that is immediately adjacent to a —$CH_3$ group, e.g., as part of a —CH(—$NR^xR^y$)—$CH_3$ moiety.

As used herein, the term "iminated ester compound" refers to a compound having the general formula: R—COO—R', where R is an optionally substituted alkyl or alkenyl group that at least contains one imino (—C(=$NR^x$)—$R^y$) substituent, R' is as defined above, and $R^x$ and $R^y$ are independently hydrogen or an organic group (e.g., alkyl, alkenyl, or aryl groups). In some such embodiments, R is an alkyl group having from 3 to 18 carbon atoms and at least one amino substituent, and R' is an unsubstituted alkyl group having from 1 to 6 carbon atoms. The compounds can have different carbon lengths for various R and R'. Further, as used herein, the term "α,ω-iminated ester compounds" refers to iminated ester compounds, as defined above, where R is an alkyl group having from 3 to 18 carbon atoms and one of the one or more imino substituents is attached to a —$CH_2$— group, e.g., as part of a —$CH_2$—C(=$NR^x$)—$R^y$ moiety. Further, as used herein, the term "α,ψ-iminated ester compounds" refers to iminated ester compounds, as defined above, where R is an alkyl group having from 3 to 18 carbon atoms and one of the one or more amino substituents is attached to a carbon atom that is immediately adjacent to a —$CH_3$ group, e.g., as part of a —CH(—C(=$NR^x$)—$R^y$)—$CH_3$ moiety.

As used herein, the term "carboxylated ester compound" refers to a compound having the general formula: R—COO—R', where R is an optionally substituted alkyl or alkenyl group that at least contains one carboxyl (—COOH) substituent, R' is as defined above, and $R^x$ and $R^y$ are independently hydrogen or an organic group (e.g., alkyl, alkenyl, or aryl groups). In some such embodiments, R is an alkyl group having from 3 to 18 carbon atoms and at least one carboxyl substituent, and R' is an unsubstituted alkyl group having from 1 to 6 carbon atoms. The compounds can have different carbon lengths for various R and R'. Further, as used herein, the term "α,ω-carboxylated ester compounds" refers to carboxylated ester compounds, as defined above, where R is an alkyl group having from 3 to 18 carbon atoms and one of the one or more carboxyl substituents is attached to a —$CH_2$— group, e.g., as part of a —$CH_2$—COOH moiety. Further, as used herein, the term "α,ψ-carboxylated ester compounds" refers to carboxylated ester compounds, as defined above, where R is an alkyl group having from 3 to 18 carbon atoms and one of the one or more carboxyl substituents is attached to a carbon atom that is immediately adjacent to a —$CH_3$ group, e.g., as part of a —CH(—COOH)—$CH_3$ moiety.

As used herein, the term "dibasic ester" refers to compounds having the general formula R'—OOC—Y—COO—R", wherein Y, R', and R" denote any organic compound (such as alkyl, aryl, or silyl groups), including those bearing heteroatom containing substituent groups. In certain embodiments, Y is a divalent saturated or unsaturated hydrocarbon, and R' and R" are alkyl, alkenyl, aryl, or alcohol groups.

As used herein, the terms "alcohol" or "alcohols" refer to compounds having the general formula: R—OH, wherein R denotes any organic moiety (such as alkyl, alkenyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. The term "hydroxyl" refers to a —OH moiety. The term "hydroxylated" refers to a moiety that bears a hydroxyl group.

As used herein, the terms "aldehyde" or "aldehydes" refer to compounds having the general formula: R—CHO, wherein R denotes any organic moiety (such as alkyl, alkenyl, aryl, or silyl groups), including those bearing heteroatom-containing substituent groups. In certain embodiments, R denotes alkyl, alkenyl, aryl, or alcohol groups. In certain embodiments, the term "aldehydes" may refer to a group of compounds with the general formula described above, wherein the compounds have different carbon lengths. The term "formyl" refers to a —CHO moiety. The term "formylated" refers to a moiety that bears a formyl group.

As used herein, the terms "acid" or "acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "acids" may refer to a group of compounds with the general formula described above, wherein the compounds have different carbon lengths. The term "carboxyl" refers to a —COOH moiety. The term "carboxylated" refers to a moiety that bears a carboxyl group.

As used herein, the terms "dibasic acid" or "diacid" refer to compounds having the general formula R'—OOC—Y—COO—R", wherein R' and R" are hydrogen, and Y denotes any organic compound (such as an alkyl, alkenyl, aryl, alcohol, or silyl group), including those bearing heteroatom substituent groups. In certain embodiments, Y is a saturated or unsaturated hydrocarbon.

As used herein, the terms “amine” or “amines” refer to compounds having the general formula: R—N(R')(R"), wherein R, R', and R" denote a hydrogen or an organic moiety (such as alkyl, aryl, or silyl groups), including those bearing heteroatom-containing substituent groups. In certain embodiments, R, R', and R" denote a hydrogen or an alkyl, alkenyl, aryl, or alcohol groups. In certain embodiments, the term “amines” may refer to a group of compounds with the general formula described above, wherein the compounds have different carbon lengths. The term “amino” refers to a —N(R)(R') moiety. The term “aminated” refers to a moiety that bears an amino group.

As used herein, the terms “imine” or “imines” refer to compounds having the general formula: R(═N—R')(—R"), wherein R, R', and R" denote a hydrogen or an organic moiety (such as alkyl, aryl, or silyl groups), including those bearing heteroatom-containing substituent groups. In certain embodiments, R, R', and R" denote a hydrogen or an alkyl, alkenyl, aryl, or alcohol groups. In certain embodiments, the term “amines” may refer to a group of compounds with the general formula described above, wherein the compounds have different carbon lengths. The term “imino” refers to a —C(═NR$^x$)—R$^y$ moiety. The term “iminated” refers to a moiety that bears an imino group.

As used herein, the term “hydrocarbon” refers to an organic group composed of carbon and hydrogen, which can be saturated or unsaturated, and can include aromatic groups.

As used herein, the terms “olefin” or “olefins” refer to compounds having at least one unsaturated carbon-carbon double bond. In certain embodiments, the term “olefins” refers to a group of unsaturated carbon-carbon double bond compounds with different carbon lengths. Unless noted otherwise, the terms “olefin” or “olefins” encompasses “polyunsaturated olefins” or “poly-olefins,” which have more than one carbon-carbon double bond. As used herein, the term “monounsaturated olefins” or “mono-olefins” refers to compounds having only one carbon-carbon double bond. In some embodiments, the olefins are alkenes, as defined below. Such alkenes can have 2 to 30 carbon atoms, or 2 to 24 carbon atoms. In some instances, the olefin can be a “terminal olefin” or “alpha-olefin,” meaning that it has a terminal carbon-carbon double bond. In some instances, the olefin can be an “internal olefin,” meaning that it does not have a terminal carbon-carbon double bond.

In some instances, the olefin can be an “alkene,” which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A “monounsaturated alkene” refers to an alkene having one carbon-carbon double bond, while a “polyunsaturated alkene” refers to an alkene having two or more carbon-carbon double bonds. A “lower alkene,” as used herein, refers to an alkene having from 2 to 8 carbon atoms.

As used herein, the term “low-molecular-weight olefin” may refer to any one or combination of unsaturated straight, branched, or cyclic hydrocarbons having 2 to 14 carbon atoms. Low-molecular-weight olefins include “alpha-olefins” or “terminal olefins,” wherein the unsaturated carbon-carbon bond is present at one end of the compound. Low-molecular-weight olefins may also include dienes or trienes. Low-molecular-weight olefins may also include internal olefins or “low-molecular-weight internal olefins.” In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, and 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. In one embodiment, it may be preferable to use a mixture of linear and branched $C_4$ olefins (i.e., combinations of: 1-butene, 2-butene, and/or isobutene). In other embodiments, a higher range of $C_{11-14}$ may be used.

As used herein, the term “mid-weight olefin” may refer to any one or combination of unsaturated straight, branched, or cyclic hydrocarbons in the $C_{15-24}$ range. Mid-weight olefins include “alpha-olefins” or “terminal olefins,” wherein the unsaturated carbon-carbon bond is present at one end of the compound. Mid-weight olefins may also include dienes or trienes. Mid-weight olefins may also include internal olefins or “mid-weight internal olefins.” In certain embodiments, it is preferable to use a mixture of olefins.

It is noted that the term olefins (including both mono- and poly-olefins) may, in some embodiments, include esters; and, in some embodiments, the esters may include olefins, if the R or R' group in the general formula R—COO—R' contains an unsaturated carbon-carbon double bond.

As used herein, “alkyl” refers to a straight or branched chain saturated hydrocarbon having 1 to 30 carbon atoms, which may be optionally substituted, as herein further described, with multiple degrees of substitution being allowed. Examples of “alkyl,” as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase “$C_{x-y}$ alkyl,” which refers to an alkyl group, as herein defined, containing from x to y, inclusive, carbon atoms. Thus, “$C_{1-6}$ alkyl” represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the “alkyl” group can be divalent, in which case the group can alternatively be referred to as an “alkylene” group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a “heteroalkyl” or “heteroalkylene” group, respectively. Non-limiting examples include “oxyalkyl” or “oxyalkylene” groups, which are groups of the following formulas: -[-(alkylene)-O-]$_x$-alkyl, or -[-(alkylene)-O-]$_x$-alkylene-, respectively, where x is 1 or more, such as 1, 2, 3, 4, 5, 6, 7, or 8. In certain embodiments, heteroalkyl can refer to protected (e.g., alkyl protected) alcohols and/or amines, such as $C_{1-6}$ alkoxy, $C_{1-6}$ alkylamino, and/or $C_{1-6}$ dialkylamino.

As used herein, “alkenyl” refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group, respectively.

As used herein, "cycloalkyl" refers to an aliphatic saturated or unsaturated hydrocarbon ring system having 1 to 20 carbon atoms, which may be optionally substituted, as herein further described, with multiple degrees of substitution being allowed. Examples of "cycloalkyl," as used herein, include, but are not limited to, cyclopropyl, cyclobutyl, cyclopentyl, cyclohexyl, cyclohexenyl, cycloheptyl, cyclooctyl, adamantyl, and the like. The number of carbon atoms in a cycloalkyl group is represented by the phrase "$C_{x-y}$ alkyl," which refers to a cycloalkyl group, as herein defined, containing from x to y, inclusive, carbon atoms. Thus, "$C_{3-10}$ cycloalkyl" represents a cycloalkyl having from 3 to 10 carbon atoms and, for example, includes, but is not limited to, cyclopropyl, cyclobutyl, cyclopentyl, cyclohexyl, cyclohexenyl, cycloheptyl, cyclooctyl, and adamantyl. In some instances, the "cycloalkyl" group can be divalent, in which case the group can alternatively be referred to as a "cycloalkylene" group. Also, in some instances, one or more of the carbon atoms in the cycloalkyl or cycloalkylene group can be replaced by a heteroatom (e.g., selected from nitrogen, oxygen, or sulfur, including N-oxides, sulfur oxides, and sulfur dioxides, where feasible), and is referred to as a "heterocycloalkyl" or "heterocycloalkylene" group, respectively.

As used herein, "alkoxy" refers to —OR, where R is an alkyl group (as defined above). The number of carbon atoms in an alkyl group is represented by the phrase "$C_{x-y}$ alkoxy," which refers to an alkoxy group having an alkyl group, as herein defined, having from x to y, inclusive, carbon atoms.

As used herein, "halogen" or "halo" refers to a fluorine, chlorine, bromine, and/or iodine atom. In some embodiments, the terms refer to fluorine and/or chlorine. As used herein, "haloalkyl" or "haloalkoxy" refer to alkyl or alkoxy groups, respectively, substituted by one or more halogen atoms. The terms "perfluoroalkyl" or "perfluoroalkoxy" refer to alkyl groups and alkoxy groups, respectively, where every available hydrogen is replaced by fluorine.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the terms "isomerization," "isomerizes," or "isomerizing" may refer to the reaction and conversion of straight-chain hydrocarbon compounds, such as normal paraffins, into branched hydrocarbon compounds, such as isoparaffins. In other embodiments, the isomerization of an olefin or an unsaturated ester indicates the shift of the carbon-carbon double bond to another location in the molecule (e.g., conversion from 9-decenoic acid to 8-decenoic acid), or it indicates a change in the geometry of the compound at the carbon-carbon double bond (e.g., cis to trans). As a non-limiting example, n-pentane may be isomerized into a mixture of n-pentane, 2-methylbutane, and 2,2-dimethylpropane. Isomerization of normal paraffins may be used to improve the overall properties of a fuel composition. Additionally, isomerization may refer to the conversion of branched paraffins into further, more branched paraffins.

As used herein, the term "diene-selective hydrogenation" or "selective hydrogenation" may refer to the targeted transformation of polyunsaturated olefins and/or esters to monounsaturated olefins and/or esters. One non-limiting example includes the selective hydrogenation of 3,6-dodecadiene to a mixture of monounsaturated products such as 1-dodecene, 2-dodecene, 3-dodecene, 4-dodecene, 5-dodecene, and/or 6-dodecene.

As used herein, the terms "conversion" or "conversion rate" may refer to the conversion from polyunsaturated olefins and/or esters into saturated esters, paraffins, monounsaturated olefins, and/or monounsaturated esters. In other words, conversion=(total polyunsaturates in the feedstock−total polyunsaturates in the product)/total polyunsaturates in the feed.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of $—CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Hydroformylation of Olefinic Esters

Certain methods disclosed herein relate to chemically transforming olefinic ester compounds, for example, by hydroformylation. In some embodiments, the methods include providing a reactant composition comprising such olefinic ester compounds. As used herein, "providing" refers broadly to any method of supplying, delivering, preparing, or otherwise making the reactant composition available. As used herein, "reactant composition" refers broadly to any composition; the modifier "reactant" is not intended to limit the range of such compositions, but merely to identify the composition as containing compounds, e.g., the olefinic ester compounds, that are intended to function as reactants in the methods disclosed herein. In some embodiments, the reactant composition consists of the olefinic ester compounds. In some other embodiments, however, the reactant composition includes the olefinic ester compounds as well as other materials. There is no particular limit to what other materials can be included in the reactant composition. For examples, in some embodiments, the reactant composition can include one or more of: hydroformylation catalysts, solvents, surfactants, and the like. The reactant composition can also contain other reactants, such as hydrogen gas and carbon monoxide, e.g., as syngas. In some embodiments, the reactant composition is substantially free of oxygen gas, e.g., containing less no more than 100 ppm oxygen, or no more than 50 ppm oxygen, or no more than 25 ppm oxygen, or no more than 10 ppm oxygen, or no more than 5 ppm oxygen, or no more than 2 ppm oxygen. In some embodiments, the reactant composition is disposed in a suitable reaction vessel, such as a reactor suitable for carrying out hydroformylation reactions.

The olefinic ester compounds can be any compounds consistent with the definition recited above, including any embodiments or combinations of embodiments thereof. In some embodiments, the olefinic ester compounds include terminal olefinic ester compounds, such as 9-decenoic acid esters, or 9,12-tridecadienoic acid esters. Such terminal olefinic ester compounds can be present in any suitable amount, e.g., relative to other olefinic ester compounds, in the reactant composition. For example, in some embodiments, the reactant composition includes at least 50% by weight, or at least 60% by weight, or at least 70% by weight, or at least 80% by weight, or at least 90% by weight, or at least 95% by weight, or at least 97% by weight, or at least 99% by weight, of terminal olefinic ester compounds, based on the total weight of olefinic ester compounds in the composition. In some other embodiments, the reactant composition can include a low amount of terminal olefinic ester compounds. For example, in some embodiments, the reactant composition includes no more than 20 percent by weight, or no more than 10 percent by weight, or no more than 7 percent by weight, or no more than 5 percent by weight, of terminal olefinic ester compounds, based on the total weight of olefinic ester compounds in the composition.

In some embodiments, such terminal olefinic ester compounds are compounds of formula (I):

(I)

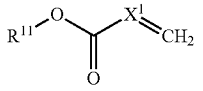

wherein:

X' is $C_{3-18}$ alkylene, $C_{3-18}$alkenylene, $C_{2-18}$ heteroalkylene, or $C_{2-18}$ heteroalkenylene, each of which is optionally substituted one or more times by substituents selected independently from $R^{12}$;

$R^{11}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{12}$; and $R^{12}$ is a halogen atom, —OH, $—NH_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $X^1$ is $C_{3-18}$ alkylene, $C_{3-18}$ alkenylene, or $C_{2-18}$ oxyalkylene, each of which is optionally substituted one or more times by substituents selected from the group consisting of a halogen atom, —OH, $—O(C_{1-6}$ alkyl), $—NH_2$, $—NH(C_{1-6}$ alkyl), and $N(C_{1-6}$ alkyl$)_2$. In some such embodiments, $X^1$ is $C_{3-18}$ alkylene, $C_{3-18}$ alkenylene, or $C_{2-18}$ oxyalkylene, each of which is optionally substituted one or more times by —OH. In some such embodiments, $X^1$ is $—(CH_2)_2—CH=$, $—(CH_2)_3—CH=$, $—(CH_2)_4—CH=$, $—(CH_2)_5—CH=$, $—(CH_2)_6—CH=$, $—(CH_2)_7—CH=$, $—(CH_2)_8—CH=$, $—(CH_2)_9—CH=$, $—(CH_2)_{10}—CH=$, $—(CH_2)_{11}—CH=$, $—(CH_2)_{12}—CH=$, $—(CH_2)_{13}—CH=$, $—(CH_2)_{14}—CH=$, or $—(CH_2)_{15}—CH=$. In some other such embodiments, $X^1$ is $—CH_2—CH=CH—CH_2—CH=$, $—(CH_2)_2—CH=CH—CH_2—CH=$, $—(CH_2)_3—CH=CH—CH_2—CH=$, $—(CH_2)_4—CH=CH—CH_2—CH=$, $—(CH_2)_5—CH=CH—CH_2—CH=$, $—(CH_2)_6—CH=CH—CH_2—CH=$, $—(CH_2)_7—CH=CH—CH_2—CH=$, $—(CH_2)_8—CH=CH—CH_2—CH=$, $—(CH_2)_9—CH=CH—CH_2—CH=$, $—(CH_2)_{10}—CH=CH—CH_2—CH=$, $—(CH_2)_{11}—CH=CH—CH_2—CH=$, or $—(CH_2)_{12}—CH=CH—CH_2—CH=$. In some other embodiments, $X^1$ is $—CH_2—CH=CH—CH_2—CH=CH—CH_2—CH=$, $—(CH_2)_2—CH=CH—CH_2—CH=CH—CH_2—CH=$, $—(CH_2)_3—CH=CH—CH_2—CH=CH—CH_2—CH=$, $—(CH_2)_4—CH=CH—CH_2—CH=CH—CH_2—CH=$, $—(CH_2)_5—CH=CH—CH_2—CH=CH—CH_2—CH=$, $—(CH_2)_6—CH=CH—CH_2—CH=CH—CH_2—CH=$, $—(CH_2)_7—CH=CH—CH_2—CH=CH—CH_2—CH=$, or $—(CH_2)_8—CH=CH—CH_2—CH=CH—CH_2—CH=$. In some embodiments, $X^1$ is $—(CH_2)_7—CH=$. In some embodiments, $X^1$ is $—(CH_2)_7—CH=CH—CH_2—CH=$.

In some embodiments, $R^{11}$ are independently $C_{1-8}$ alkyl, $C_{2-8}$ alkenyl, or $C_{1-8}$ oxyalkyl, each of which is optionally substituted one or more times by —OH or —CHO. In some other embodiments, $R^{11}$ is methyl, ethyl, propyl, isopropyl, butyl, isobutyl, sec-butyl, tert-butyl, pentyl, tert-pentyl, neopentyl, hexyl, or 2-ethylhexyl. In some other embodiments, $R^{11}$ is methyl or ethyl. In some other embodiments, $R^{11}$ is methyl.

In some embodiments, the olefinic ester compounds include internal olefinic ester compounds, such as 9-dodecenoic acid esters. Such internal olefinic ester compounds can be present in any suitable amount, e.g., relative to other olefinic ester compounds, in the reactant composition. For example, in some embodiments, the reactant composition includes at least 5% by weight, or at least 10% by weight, or at least 15% by weight, or at least 20% by weight, or at least 25% by weight, or at least 30% by weight, or at least 35% by weight, or at least 40% by weight, or at least 45% by weight, or at least 50% by weight, of internal olefinic ester compounds, based on the total weight of olefinic ester compounds in the composition.

In some embodiments, such internal olefinic ester compounds are compounds of formula (II):

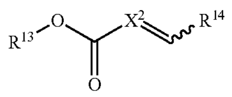

(II)

wherein:

$X^2$ is $C_{3-18}$ alkylene, $C_{3-18}$ alkenylene, $C_{2-18}$ heteroalkylene, or $C_{2-18}$ heteroalkenylene, each of which is optionally substituted one or more times by substituents selected independently from $R^{15}$;

$R^{13}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{15}$;

$R^{14}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{15}$; and $R^{15}$ is a halogen atom, —OH, —$NH_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $X^2$ is $C_{3-18}$ alkylene, $C_{3-18}$ alkenylene, or $C_{2-18}$ oxyalkylene, each of which is optionally substituted one or more times by substituents selected from the group consisting of a halogen atom, —OH, —O($C_{1-6}$ alkyl), —$NH_2$, —NH($C_{1-6}$ alkyl), and N($C_{1-6}$ alkyl)$_2$. In some embodiments, $X^2$ is $C_{3-18}$ alkylene, $C_{3-18}$ alkenylene, or $C_{2-18}$ oxyalkylene, each of which is optionally substituted one or more times by —OH. In some embodiments, $X^2$ is $-(CH_2)_2-CH=$, $-(CH_2)_3-CH=$, $-(CH_2)_4-CH=$, $-(CH_2)_5-CH=$, $-(CH_2)_6-CH=$, $-(CH_2)_7-CH=$, $-(CH_2)_8-CH=$, $-(CH_2)_9-CH=$, $-(CH_2)_{10}-CH=$, $-(CH_2)_{11}-CH=$, $-(CH_2)_{12}-CH=$, $-(CH_2)_{13}-CH=$, $-(CH_2)_{14}-CH=$, or $-(CH_2)_{15}-CH=$. In some embodiments, $X^2$ is $-(CH_2)_7-CH=$.

In some embodiments, $R^{13}$ is $C_{1-8}$ alkyl, $C_{2-8}$ alkenyl, or $C_{1-8}$ oxyalkyl, each of which is optionally substituted one or more times by —OH or —CHO. In some embodiments, $R^{13}$ is methyl, ethyl, propyl, isopropyl, butyl, isobutyl, sec-butyl, tert-butyl, pentyl, tert-pentyl, neopentyl, hexyl, or 2-ethylhexyl. In some embodiments, $R^{13}$ is methyl or ethyl. In some embodiments, $R^{13}$ is methyl.

In some embodiments, $R^{14}$ is $C_{1-8}$ alkyl, $C_{2-8}$ alkenyl, or $C_{1-8}$ oxyalkyl, each of which is optionally substituted one or more times by —OH. In some embodiments, $R^{14}$ is methyl, ethyl, propyl, butyl, pentyl, hexyl, heptyl, octyl, or nonyl. In some embodiments, $R^{14}$ is methyl or ethyl. In some embodiments, $R^{14}$ is ethyl. In some embodiments, $R^{14}$ is methyl.

In some embodiments, including some described above, the reactant composition includes both terminal olefinic ester compounds and internal olefinic ester compounds. These two classes of olefinic ester compounds can be present in the reactant composition in any suitable relative amounts. In some embodiments, the weight-to-weight ratio of terminal olefinic ester compounds to internal olefinic ester compounds is from 1:500 to 500:1, or from 1:300 to 300:1, or from 1:200 to 200:1, or from 1:100 to 100:1, or from 1:50 to 50:1, or from 1:40 to 40:1, or from 1:20 to 20:1, or from 1:10 to 10:1, or from 1:5 to 5:1, or from 1:3 to 3:1, or from 1:2 to 2:1.

In some embodiments, the reactant composition includes monounsaturated olefinic ester compounds, such as 9-decenoic acid esters or 9-dodecenoic acid esters. Such monounsaturated olefinic ester compounds can be present in any suitable amount, e.g., relative to other olefinic ester compounds, in the reactant composition. For example, in some embodiments, the reactant composition includes at least 30% by weight, or at least 40% by weight, or at least 50% by weight, or at least 60% by weight, or at least 70% by weight, or at least 80% by weight, or at least 90% by weight, or at least 95% by weight, of monounsaturated olefinic ester compounds, based on the total weight of olefinic ester compounds in the composition. In some embodiments, the reactant composition includes no more than 10% by weight, or no more than 20% by weight, or no more than 30% by weight, or no more than 40% by weight, or no more than 50% by weight, or no more than 60% by weight, or no more than 70% by weight, of monounsaturated olefinic ester compounds, based on the total weight of olefinic ester compounds in the composition.

In some embodiments, the reactant composition includes polyunsaturated olefinic ester compounds, such as diunsaturated olefinic ester compounds, e.g., 9,12-tridecadienoic acid esters. Such polyunsaturated olefinic ester compounds can be present in any suitable amount, e.g., relative to other olefinic ester compounds, in the reactant composition. For example, in some embodiments, the reactant composition includes at least 30% by weight, or at least 40% by weight, or at least 50% by weight, or at least 60% by weight, or at least 70% by weight, or at least 80% by weight, or at least 90% by weight, or at least 95% by weight, of polyunsaturated olefinic ester compounds, based on the total weight of olefinic ester compounds in the composition. In some embodiments, the reactant composition includes no more than 10% by weight, or no more than 20% by weight, or no more than 30% by weight, or no more than 40% by weight, or no more than 50% by weight, or no more than 60% by weight, or no more than 70% by weight, of polyunsaturated olefinic ester compounds, based on the total weight of olefinic ester compounds in the composition.

In some embodiments, the olefinic ester compounds, or at least a portion of the olefinic ester compounds, are derived from a renewable source, such as a natural oil (including natural oil derivatives). Any suitable process for carrying out such a derivation can be used, including, but not limited to, biological or biochemical processes (e.g., fermentation, enzymatic processes, etc.) and chemical processes (e.g., metathesis). In some embodiments, the olefinic ester compounds are derived from a process that includes metathesis of a feedstock that contains a natural oil. Such processes are described in further detail below.

The reactant composition can include further ingredients in addition to the olefinic ester compounds. In some embodiments, the reactant composition includes a carrier. In some such embodiments, the carrier has a single phase, such as a nonpolar phase. In some other embodiments, the carrier has two or more phases, where at least one of the phases is a polar phase and at least one of the phases is a nonpolar phase. The above-mentioned polar phases can employ any suitable polar solvents or mixtures thereof. Suitable polar solvents include, but are not limited to, short-chain alcohols (e.g., methanol, ethanol, propanol, isopropanol, butanol, etc.), water, acetone, N,N-dimethylformamide (DMF), acetonitrile, and dimethyl sulfoxide (DMSO). Suitable nonpolar solvents include, but are not limited to, hydrocarbons (e.g., pentane, hexane, heptane, cyclohexane, benzene, toluene, xylenes, etc.), halocarbons (e.g., chloroform, carbon tetrachloride, etc.), and diethyl ether. Some other solvents can be either polar or nonpolar, for example, depending on their use. These include, but are not limited to, methylene chloride, tetrahydrofuran (THF), and ethyl acetate.

In some embodiments, the reactant composition further comprises a hydroformylation catalyst. Any suitable hydroformylation catalyst can be used. Various hydroformylation catalysts are described in further detail below.

The methods disclosed herein include reacting olefinic ester compounds with hydrogen gas and carbon monoxide (e.g., as syngas) to form a product composition that includes formylated ester compounds or hydroxylated ester compounds. When an olefinic compound reacts with $H_2$ and CO in the presence of certain catalysts (e.g., hydroformylation catalysts), the reaction can result in either aldehydes and/or alcohols. One type of reaction product may be preferred over the other under certain reaction conditions. For example, under higher pressures and/or temperatures, alcohols may be preferred, whereas aldehydes may be preferred under "softer" reaction conditions. One can therefore adjust the reaction conditions, the catalyst, and the like for a particular type of olefinic input to obtain the desired relative quantities of aldehydes and alcohols. Hydroformylation methods are discussed in further detail below.

In some embodiments, the methods disclosed herein lead to a product composition that comprises one or more formylated ester compounds. In some such embodiments, the formylated ester compounds are compounds of formula (III):

(III)

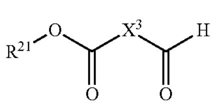

wherein:

$X^3$ is $C_{3-18}$ alkylene, $C_{3-18}$ alkenylene, $C_{2-18}$ heteroalkylene, or $C_{2-18}$ heteroalkenylene, each of which is optionally substituted one or more times by substituents selected independently from $R^{22}$;

$R^{21}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{22}$; and $R^{22}$ is a halogen atom, —OH, —$NH_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $X^3$ is $C_{3-18}$ alkylene, $C_{3-18}$ alkenylene, or $C_{2-18}$ oxyalkylene, each of which is optionally substituted one or more times by substituents selected from the group consisting of a halogen atom, —OH, —O($C_{1-6}$ alkyl), —$NH_2$, —NH($C_{1-6}$ alkyl), and N($C_{1-6}$ alkyl)$_2$. In some other embodiments, $X^3$ is $C_{3-18}$ alkylene, $C_{3-18}$ alkenylene, or $C_{2-18}$ oxyalkylene, each of which is optionally substituted one or more times by —OH. In some further embodiments, $X^3$ is —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, or —$(CH_2)_{16}$—. In some other embodiments, $X^3$ is —$CH_2$—CH═CH—$CH_2$—$CH_2$—, —$(CH_2)_2$—CH═CH—$CH_2$—$CH_2$—, —$(CH_2)_3$—CH═CH—$CH_2$—$CH_2$—, —$(CH_2)_4$—CH═CH—$CH_2$—$CH_2$—, —$(CH_2)_5$—CH═CH—$CH_2$—$CH_2$—, —$(CH_2)_6$—CH═CH—$CH_2$—$CH_2$—, —$(CH_2)_7$—CH═CH—$CH_2$—$CH_2$—, —$(CH_2)_8$—CH═CH—$CH_2$—$CH_2$—, —$(CH_2)_9$—CH═CH—$CH_2$—$CH_2$—, —$(CH_2)_{10}$—CH═CH—$CH_2$—$CH_2$—, —$(CH_2)_{11}$—CH═CH—$CH_2$—$CH_2$—, or —$(CH_2)_{12}$—CH═CH—$CH_2$—$CH_2$—. In some embodiments, $X^3$ is —$CH_2$—CH═CH—$CH_2$—CH═CH—$CH_2$—$CH_2$—, —$(CH_2)_2$—CH═CH—$CH_2$—CH═CH—$CH_2$—$CH_2$—, —$(CH_2)_3$—CH═CH—$CH_2$—CH═CH—$CH_2$—$CH_2$—, —$(CH_2)_4$—CH═CH—$CH_2$—CH═CH—$CH_2$—$CH_2$—, —$(CH_2)_5$—CH═CH—$CH_2$—CH═CH—$CH_2$—$CH_2$—, —$(CH_2)_6$—CH═CH—$CH_2$—CH═CH—$CH_2$—$CH_2$—, —$(CH_2)_7$—CH═CH—$CH_2$—CH═CH—$CH_2$—$CH_2$—, or —$(CH_2)_8$—CH═CH—$CH_2$—CH═CH—$CH_2$—$CH_2$—.

In some embodiments, $R^{21}$ is $C_{1-8}$ alkyl, $C_{2-8}$ alkenyl, or $C_{1-8}$ oxyalkyl, each of which is optionally substituted one or more times by —OH or —CHO. In some other embodiments, $R^{21}$ is methyl, ethyl, propyl, isopropyl, butyl, isobutyl, sec-butyl, tert-butyl, pentyl, tert-pentyl, neopentyl, hexyl, or 2-ethylhexyl. In some embodiments, $R^{21}$ is methyl.

In some embodiments, the product composition, which includes one or more formylated ester compounds, includes non-hydroxylated formylated ester compounds and, optionally, one or more hydroxylated formylated ester compounds. In some such embodiments, the weight-to-weight ratio of non-hydroxylated formylated ester compounds to hydroxylated formylated ester compounds in the product composition is at least 10:1, or at least 15:1, or at least 20:1, or at least 25:1, or at least 35:1, or at least 50:1, or at least 100:1. In some embodiments, the formylated ester compounds are α,ω-formylated ester compounds. In some such embodiments, the α,ω-formylated ester compounds comprise esters of 10-formyldecanoic acid, such as alkyl esters of 10-formyldecanoic acid. In some other embodiments, the formylated ester compounds are α,ψ-formylated ester compounds. In some such embodiments, the α,ψ-formylated ester compounds comprise esters of 9-formyldecanoic acid, such as alkyl esters of 9-formyldecanoic acid.

In some embodiments, it can be desirable to separate at least a portion of any non-hydroxylated formylated ester compounds from other components in the product composition. Thus, in some further embodiments of any of the above embodiments, the method includes separating at least a portion of the non-hydroxylated formylated ester compounds from other components in the product composition. Separating such compounds from other components in the product stream may allow them to be used more suitable for particular applications, or more suitable for further modification.

Hydroformylation of Olefins

Certain methods disclosed herein relate to chemically transforming olefins, for example, by hydroformylation. While the term "olefin" broadly includes compounds that are functionalized by certain heteroatom-containing functional groups, in some embodiments, the term refers to unfunctionalized hydrocarbons that contain at least one carbon-carbon double bond. Thus, whenever the term "olefin" or "olefins" is used in this section, the term is intended to describe such hydrocarbyl olefins, as well as the broader class of olefins.

In some embodiments, the methods include providing a reactant composition comprising such olefins. As used herein, "providing" refers broadly to any method of supplying, delivering, preparing, or otherwise making the reactant composition available. As used herein, "reactant composition" refers broadly to any composition; the modifier "reactant" is not intended to limit the range of such compositions, but merely to identify the composition as containing compounds, e.g., the olefins, that are intended to function as reactants in the methods disclosed herein. In some embodiments, the reactant composition consists of the olefins. In some other embodiments, however, the reactant composition includes the olefins as well as other materials. There is no particular limit to what other materials can be included in the reactant composition. For examples, in some embodiments, the reactant composition can include one or more of: hydroformylation catalysts, solvents, surfactants, and the like. The reactant composition can also contain other reactants, such as hydrogen gas and carbon monoxide, e.g., as syngas. In some embodiments, the reactant composition is substantially free of oxygen gas, e.g., containing less no more than 100 ppm oxygen, or no more than 50 ppm oxygen, or no more than 25 ppm oxygen, or no more than 10 ppm oxygen, or no more than 5 ppm oxygen, or no more than 2 ppm oxygen. In some embodiments, the reactant composition is disposed in a suitable reaction vessel, such as a reactor suitable for carrying out hydroformylation reactions.

The olefins can be any compounds consistent with the definition recited above, including any embodiments or combinations of embodiments thereof. In some embodiments, the olefins include terminal olefins, such as 1-decene, or 1,4-decadiene. Such terminal olefins can be present in any suitable amount, e.g., relative to other olefins, in the reactant composition. For example, in some embodiments, the reactant composition includes at least 50% by weight, or at least 60% by weight, or at least 70% by weight, or at least 80% by weight, or at least 90% by weight, or at least 95% by weight, or at least 97% by weight, or at least 99% by weight, of terminal olefins, based on the total weight of olefins in the composition.

In some embodiments, such terminal olefins are compounds of formula (IV):

$$H_2C{=}X^4 \qquad \text{(IV)}$$

wherein:

$X^4$ is $C_{3-18}$ alkyl, $C_{3-18}$ alkenyl, $C_{2-18}$ heteroalkyl, or $C_{2-18}$ heteroalkenyl, each of which is optionally substituted one or more times by substituents selected independently from $R^{41}$; and $R^{41}$ is a halogen atom, —OH, —$NH_2$, $C_{3-10}$ cycloalkyl, or $C_{2-10}$ heterocycloalkyl.

In some such embodiments, $X^4$ is $C_{3-18}$ alkyl, $C_{3-18}$ alkenyl, or $C_{2-18}$ oxyalkyl, each of which is optionally substituted one or more times by substituents selected from the group consisting of a halogen atom, —OH, —O($C_{1-6}$ alkyl), —$NH_2$, —NH($C_{1-6}$ alkyl), and —N($C_{1-6}$ alkyl)$_2$. In some embodiments, $X^4$ is $C_{3-18}$ alkyl, $C_{3-18}$ alkenyl, or $C_{2-18}$ oxyalkyl, each of which is optionally substituted one or more times by —OH. In some further embodiments, $X^4$ is $=CH-(CH_2)_2-CH_3$, $=CH-(CH_2)_3-CH_3$, $=CH-(CH_2)_4-CH_3$, $=CH-(CH_2)_5-CH_3$, $=CH-(CH_2)_6-CH_3$, $=CH-(CH_2)_7-CH_3$, $=CH-(CH_2)_5-CH_3$, $=CH-(CH_2)_9-CH_3$, $=CH-(CH_2)_{10}-CH_3$, $=CH-(CH_2)_{11}-CH_3$, $=CH-(CH_2)_{12}-CH_3$, $=CH-(CH_2)_{13}-CH_3$, $=CH-(CH_2)_{14}-CH_3$, or $=CH-(CH_2)_{15}-CH_3$. In some embodiments, $X^4$ is $=CH-CH_2-CH=CH-CH_2-CH_3$, $=CH-CH_2-CH=CH-(CH_2)_2-CH_3$, $=CH-CH_2-CH=CH-(CH_2)_3-CH_3$, $=CH-CH_2-CH=CH-(CH_2)_4-CH_3$, $=CH-CH_2-CH=CH-(CH_2)_5-CH_3$, $=CH-CH_2-CH=CH-(CH_2)_6-CH_3$, $=CH-CH_2-CH=CH-(CH_2)_7-CH_3$, $=CH-CH_2-CH=CH-(CH_2)_5-CH_3$, $=CH-CH_2-CH=CH-(CH_2)_9-CH_3$, $=CH-CH_2-CH=CH-(CH_2)_{10}-CH_3$, $=CH-CH_2-CH=CH-(CH_2)_{11}-CH_3$, or $=CH-CH_2-CH=CH-(CH_2)_{12}-CH_3$. In some embodiments, $X^4$ is $=CH-CH_2-CH=CH-CH_2-CH=CH-CH_2-CH_3$, $=CH-CH_2-CH=CH-CH_2-CH=CH-(CH_2)_2-CH_3$, $=CH-CH_2-CH=CH-CH_2-CH=CH-(CH_2)_3-CH_3$, $=CH-CH_2-CH=CH-CH_2-CH=CH-(CH_2)_4-CH_3$, $=CH-CH_2-CH=CH-CH_2-CH=CH-(CH_2)_5-CH_3$, $=CH-CH_2-CH=CH-CH_2-CH=CH-(CH_2)_6-CH_3$, $=CH-CH_2-CH=CH-CH_2-CH=CH-(CH_2)_7-CH_3$, $=CH-CH_2-CH=CH-CH_2-CH=CH-(CH_2)_5-CH_3$; or $=CH-CH_2-CH=CH-CH_2-CH=CH-(CH_2)_9-CH_3$. In some embodiments, $X^4$ is $=CH-(CH_2)_7-CH_3$. In some embodiments, $X^4$ is $=CH-CH_2-CH=CH-(CH_2)_7-CH_3$. In some embodiments, $X^4$ is $=CH-CH_2-CH=CH-CH_2-CH=CH-(CH_2)_7-CH_3$.

In some embodiments, the olefins include internal olefins, such as 3-dodecene. Such internal olefins can be present in any suitable amount, e.g., relative to other olefins, in the reactant composition. For example, in some embodiments, the reactant composition includes at least 5% by weight, or at least 10% by weight, or at least 15% by weight, or at least 20% by weight, or at least 25% by weight, or at least 30% by weight, or at least 35% by weight, or at least 40% by weight, or at least 45% by weight, or at least 50% by weight, of internal olefins, based on the total weight of olefins in the composition.

In some embodiments, such internal olefins are compounds of formula (V):

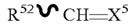

(V)

wherein:

$X^5$ is $C_{3-18}$ alkyl, $C_{3-18}$ alkenyl, $C_{2-18}$ heteroalkyl, or $C_{2-18}$ heteroalkenyl, each of which is optionally substituted one or more times by substituents selected independently from $R^{51}$;

$R^{51}$ is a halogen atom, —OH, —$NH_2$, $C_{3-10}$ cycloalkyl, or $C_{2-10}$ heterocycloalkyl; and $R^{52}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{51}$, or $R^{52}$ can optionally combine with $X^5$ to form an unsaturated cyclic group, such as a cycloalkylene group (e.g., cyclohexylene).

In some embodiments, $X^5$ is $C_{3-18}$ alkyl, $C_{3-18}$ alkenyl, or $C_{2-18}$ oxyalkyl, each of which is optionally substituted one or more times by substituents selected from the group consisting of a halogen atom, —OH, —O($C_{1-6}$ alkyl), —$NH_2$, —NH($C_{1-6}$ alkyl), and —N($C_{1-6}$ alkyl)$_2$. In some embodiments, $X^5$ is $C_{3-18}$ alkyl, $C_{3-18}$ alkenyl, or $C_{2-18}$ oxyalkyl, each of which is optionally substituted one or more times by —OH. In some embodiments, $X^5$ is =CH—$(CH_2)_2$—$CH_3$, =CH—$(CH_2)_3$—$CH_3$, =CH—$(CH_2)_4$—$CH_3$, =CH—$(CH_2)_5$—$CH_3$, =CH—$(CH_2)_6$—$CH_3$, =CH—$(CH_2)_7$—$CH_3$, =CH—$(CH_2)_8$—$CH_3$, =CH—$(CH_2)_9$—$CH_3$, =CH—$(CH_2)_{10}$—$CH_3$, =CH—$(CH_2)_{11}$—$CH_3$, =CH—$(CH_2)_{12}$—$CH_3$, =CH—$(CH_2)_{13}$—$CH_3$, =CH—$(CH_2)_{14}$—$CH_3$, or =CH—$(CH_2)_{15}$—$CH_3$. In some embodiments, $X^5$ is =CH—$CH_2$—CH=CH—$CH_2$—$CH_3$, =CH—$CH_2$—CH=CH—$(CH_2)_2$—$CH_3$, =CH—$CH_2$—CH=CH—$(CH_2)_3$—$CH_3$, =CH—$CH_2$—CH=CH—$(CH_2)_4$—$CH_3$, =CH—$CH_2$—CH=CH—$(CH_2)_5$—$CH_3$, =CH—$CH_2$—CH=CH—$(CH_2)_6$—$CH_3$, =CH—$CH_2$—CH=CH—$(CH_2)_7$—$CH_3$, =CH—$CH_2$—CH=CH—$(CH_2)_8$—$CH_3$, =CH—$CH_2$—CH=CH—$(CH_2)_9$—$CH_3$, =CH—$CH_2$—CH=CH—$(CH_2)_{10}$—$CH_3$, =CH—$CH_2$—CH=CH—$(CH_2)_{11}$—$CH_3$, or =CH—$CH_2$—CH=CH—$(CH_2)_{12}$—$CH_3$. In some embodiments, $X^5$ is =CH—$CH_2$—CH=CH—$CH_2$—CH=CH—$CH_2$—$CH_3$, =CH—$CH_2$—CH=CH—$CH_2$—CH=CH—$(CH_2)_2$—$CH_3$, =CH—$CH_2$—CH=CH—$CH_2$—CH=CH—$(CH_2)_3$—$CH_3$, =CH—$CH_2$—CH=CH—$CH_2$—CH=CH—$(CH_2)_4$—$CH_3$, =CH—$CH_2$—CH=CH—$CH_2$—CH=CH—$(CH_2)_5$—$CH_3$, =CH—$CH_2$—CH=CH—$CH_2$—CH=CH—$(CH_2)_6$—$CH_3$, =CH—$CH_2$—CH=CH—$CH_2$—CH=CH—$(CH_2)_7$—$CH_3$, =CH—$CH_2$—CH=CH—$CH_2$—CH=CH—$(CH_2)_8$—$CH_3$, or =CH—$CH_2$—CH=CH—$CH_2$—CH=CH—$(CH_2)_9$—$CH_3$. In some embodiments, $X^5$ is =CH—$(CH_2)_7$—$CH_3$. In some embodiments, $X^5$ is =CH—$CH_2$—CH=CH—$(CH_2)_7$—$CH_3$. In some embodiments, $X^5$ is =CH—$CH_2$—CH=CH—$CH_2$—CH=CH—$(CH_2)_7$—$CH_3$.

In some embodiments, $R^{52}$ is $C_{1-8}$ alkyl, $C_{2-8}$ alkenyl, or $C_{1-8}$ oxyalkyl, each of which is optionally substituted one or more times by —OH or —CHO. In some other embodiments, $R^{52}$ is methyl, ethyl, propyl, butyl, pentyl, hexyl, heptyl, octyl, or nonyl. In some further embodiments, $R^{52}$ is methyl or ethyl.

In some embodiments, including some described above, the reactant composition includes both terminal olefins and internal olefins. These two classes of olefins can be present in the reactant composition in any suitable relative amounts. In some embodiments, the weight-to-weight ratio of terminal olefins to internal olefins is from 1:500 to 500:1, or from 1:300 to 300:1, or from 1:200 to 200:1, or from 1:100 to 100:1, or from 1:50 to 50:1, or from 1:40 to 40:1, or from 1:20 to 20:1, or from 1:10 to 10:1, or from 1:5 to 5:1, or from 1:3 to 3:1, or from 1:2 to 2:1.

In some embodiments, the reactant composition includes monounsaturated olefins, such as 1-decene or 3-dodecene. Such monounsaturated olefins can be present in any suitable amount, e.g., relative to other olefins, in the reactant composition. For example, in some embodiments, the reactant composition includes at least 30% by weight, or at least 40% by weight, or at least 50% by weight, or at least 60% by weight, or at least 70% by weight, or at least 80% by weight, or at least 90% by weight, or at least 95% by weight, of monounsaturated olefins, based on the total weight of olefins in the composition. In some embodiments, the reactant composition includes no more than 10% by weight, or no more than 20% by weight, or no more than 30% by weight, or no more than 40% by weight, or no more than 50% by weight, or no more than 60% by weight, or no more than 70% by weight, of monounsaturated olefins, based on the total weight of olefins in the composition.

In some embodiments, the reactant composition includes polyunsaturated olefins, such as diunsaturated olefins, e.g., 1,4-decadiene. Such polyunsaturated olefins can be present in any suitable amount, e.g., relative to other olefins, in the reactant composition. For example, in some embodiments, the reactant composition includes at least 30% by weight, or at least 40% by weight, or at least 50% by weight, or at least 60% by weight, or at least 70% by weight, or at least 80% by weight, or at least 90% by weight, or at least 95% by weight, of polyunsaturated olefins, based on the total weight of olefins in the composition. In some embodiments, the reactant composition includes no more than 10% by weight, or no more than 20% by weight, or no more than 30% by weight, or no more than 40% by weight, or no more than 50% by weight, or no more than 60% by weight, or no more than 70% by weight, of polyunsaturated olefins, based on the total weight of olefins in the composition.

In some embodiments, the olefins, or at least a portion of the olefins, are derived from a renewable source, such as a natural oil (including natural oil derivatives). Any suitable process for carrying out such a derivation can be used, including, but not limited to, biological or biochemical processes (e.g., fermentation, enzymatic processes, etc.) and chemical processes (e.g., metathesis). In some embodiments, the olefins are derived from a process that includes metathesis of a feedstock that contains a natural oil. Such processes are described in further detail below.

The reactant composition can include further ingredients in addition to the olefins. In some embodiments, the reactant composition includes a carrier. In some such embodiments, the carrier has a single phase, such as a nonpolar phase. In some other embodiments, the carrier has two or more phases, where at least one of the phases is a polar phase and at least one of the phases is a nonpolar phase. The above-mentioned polar phases can employ any suitable polar solvents or mixtures thereof. Suitable polar solvents include, but are not limited to, short-chain alcohols (e.g., methanol, ethanol, propanol, isopropanol, butanol, etc.), water, acetone, N,N-dimethylformamide (DMF), acetonitrile, and dimethyl sulfoxide (DMSO). Suitable nonpolar solvents include, but are not limited to, hydrocarbons (e.g., pentane, hexane, heptane, cyclohexane, benzene, toluene, xylenes, etc.), halocarbons (e.g., chloroform, carbon tetrachloride, etc.), and diethyl ether. Some other solvents can be either polar or nonpolar, for example, depending on their use. These include, but are not limited to, methylene chloride, tetrahydrofuran (THF), and ethyl acetate.

In some embodiments, the reactant composition further comprises a hydroformylation catalyst. Any suitable hydroformylation catalyst can be used. Various hydroformylation catalysts are described in further detail below.

The methods disclosed herein include reacting olefins with hydrogen gas and carbon monoxide (e.g., as syngas) to form a product composition that includes aldehydes or alcohols. When an olefinic compound reacts with $H_2$ and CO in the presence of certain catalysts (e.g., hydroformylation catalysts), the reaction can result in either aldehydes and/or alcohols. One type of reaction product may be preferred over the other under certain reaction conditions. For example, under higher pressures and/or temperatures, alcohols may be preferred, whereas aldehydes may be preferred under "softer" reaction conditions. One can therefore adjust the reaction conditions, the catalyst, and the like for a particular type of olefinic input to obtain the desired relative quantities of aldehydes and alcohols. Hydroformylation methods are discussed in further detail below.

In some embodiments, the methods disclosed herein lead to a product composition that comprises one or more formylated ester compounds. In some such embodiments, the formylated ester compounds are compounds of formula (VI):

$$X^6—CHO \quad (VI)$$

wherein:

$X^6$ is $C_{3-18}$ alkyl, $C_{3-18}$ alkenyl, $C_{2-18}$ heteroalkyl, $C_{2-18}$ heteroalkenyl, or a $C_{3-18}$ cycloalkyl group, each of which is optionally substituted one or more times by substituents selected independently from $R^{61}$; and $R^{61}$ is a halogen atom, —OH, —$NH_2$, $C_{3-10}$ cycloalkyl, $C_{2-10}$ heterocycloalkyl, or $C_{1-12}$ alkyl.

In some embodiments, $X^6$ is $C_{3-18}$ alkyl, $C_{3-18}$ alkenyl, or $C_{2-18}$ oxyalkyl, each of which is optionally substituted one or more times by substituents selected from the group consisting of a halogen atom, —OH, —O($C_{1-6}$ alkyl), —$NH_2$, —NH($C_{1-6}$ alkyl), and N($C_{1-6}$ alkyl)$_2$. In some other embodiments, $X^6$ is $C_{3-18}$ alkyl, $C_{3-18}$ alkenyl, or $C_{2-18}$ oxyalkyl, each of which is optionally substituted one or more times by —OH or —CHO. In some further embodiments, $X^6$ is —$(CH_2)_2$—$CH_3$, —$(CH_2)_3$—$CH_3$, —$(CH_2)_4$—$CH_3$, —$(CH_2)_5$—$CH_3$, —$(CH_2)_6$—$CH_3$, —$(CH_2)_7$—$CH_3$, —$(CH_2)_8$—$CH_3$, —$(CH_2)_9$—$CH_3$, —$(CH_2)_{10}$—$CH_3$, —$(CH_2)_{11}$—$CH_3$, —$(CH_2)_{12}$—$CH_3$, —$(CH_2)_{13}$—$CH_3$, —$(CH_2)_{14}$—$CH_3$, —$(CH_2)_{15}$—$CH_3$, —$(CH_2)_{16}$—$CH_3$, or —$(CH_2)_{17}$—$CH_3$. In some other embodiments, $X^6$ is —$CH_2$—$CH_2$—CH═CH—$CH_2$—$CH_3$, —$CH_2$—$CH_2$—CH═CH—$(CH_2)_2$—$CH_3$, —$CH_2$—$CH_2$—CH═CH—$(CH_2)_3$—$CH_3$, —$CH_2$—$CH_2$—CH═CH—$(CH_2)_4$—$CH_3$, —$CH_2$—$CH_2$—CH═CH—$(CH_2)_5$—$CH_3$, —$CH_2$—$CH_2$—CH═CH—$(CH_2)_6$—$CH_3$, —$CH_2$—$CH_2$—CH═CH—$(CH_2)_7$—$CH_3$, —$CH_2$—$CH_2$—CH═CH—$(CH_2)_8$—$CH_3$, —$CH_2$—$CH_2$—CH═CH—$(CH_2)_9$—$CH_3$, —$CH_2$—$CH_2$—CH═CH—$(CH_2)_{10}$—$CH_3$, —$CH_2$—$CH_2$—CH═CH—$(CH_2)_{11}$—$CH_3$, —$CH_2$—$CH_2$—CH═CH—$(CH_2)_{12}$—$CH_3$, or —$CH_2$—$CH_2$—CH═CH—$(CH_2)_{13}$—$CH_3$. In some further embodiments, $X^6$ is —$CH_2$—$CH_2$—CH═CH—$CH_2$—CH═CH—$CH_2$—$CH_3$, —$CH_2$—$CH_2$—CH═CH—$CH_2$—CH═CH—$(CH_2)_2$—$CH_3$, —$CH_2$—$CH_2$—CH═CH—$CH_2$—CH═CH—$(CH_2)_3$—$CH_3$, —$CH_2$—$CH_2$—CH═CH—$CH_2$—CH═CH—$(CH_2)_4$—$CH_3$, —$CH_2$—$CH_2$—CH═CH—$CH_2$—CH═CH—$(CH_2)_5$—$CH_3$, —$CH_2$—$CH_2$—CH═CH—$CH_2$—CH═CH—$(CH_2)_6$—$CH_3$, —$CH_2$—$CH_2$—CH═CH—$CH_2$—CH═CH—$(CH_2)_7$—$CH_3$, —$CH_2$—$CH_2$—CH═CH—$CH_2$—CH═CH—$(CH_2)_8$—$CH_3$, —$CH_2$—$CH_2$—CH═CH—$CH_2$—CH═CH—$(CH_2)_9$—$CH_3$, or —$CH_2$—$CH_2$—CH═CH—$CH_2$—CH═CH—$(CH_2)_{10}$—$CH_3$. In some embodiments, $X^6$ is —$(CH_2)_9$—$CH_3$. In some embodiments, $X^6$ is —$CH_2$—$CH_2$—CH═CH—$(CH_2)_5$—$CH_3$. In some embodiments, $X^6$ is —$CH_2$—$CH_2$—CH═CH—$CH_2$—CH═CH—$(CH_2)_2$—$CH_3$.

In some embodiments, the product composition, which includes one or more aldehydes, includes non-hydroxylated aldehydes and, optionally, one or more alcohols. In some such embodiments, the weight-to-weight ratio of non-hydroxylated aldehydes to hydroxylated aldehydes in the product composition is at least 10:1, or at least 15:1, or at least 20:1, or at least 25:1, or at least 35:1, or at least 50:1, or at least 100:1. In some embodiments, the aldehydes are normal aldehydes, meaning that the formyl group is formed on the terminal carbon atom of a terminal carbon-carbon double bond of the olefin. In some such embodiments, the normal aldehydes include 1-undecanal. In some other embodiments, the aldehydes are iso aldehydes, meaning that the formyl group is formed on a non-terminal carbon atom of the carbon-carbon double bond. In some such embodiments, the iso aldehydes include 2-methyl-1-decanal.

In some embodiments, it can be desirable to separate at least a portion of any non-hydroxylated aldehydes from other components in the product composition. Thus, in some further embodiments of any of the above embodiments, the method includes separating at least a portion of the non-hydroxylated aldehydes from other components in the product composition. Separating such compounds from other components in the product stream may allow them to be used more suitable for particular applications, or more suitable for further modification.

Hydroformylation

The methods disclosed herein include reacting certain olefinic compounds with hydrogen gas and CO, e.g., in the presence of a hydroformylation catalyst. In some embodiments, the olefinic compounds are functionalized olefins, such as the olefinic ester compounds disclosed above. In some other embodiments, the olefinic compounds are olefins, such as alkenes, e.g., hydrocarbons containing carbon-carbon double bonds. Such reactions can be referred to generally as "hydroformylation," and the processing steps can be referred to as "hydroformylating" an olefinic compound.

In general, hydroformylation includes reacting olefinic compounds in the presence of a hydroformylation catalyst to add an aldehyde group and a hydrogen atom to a carbon-carbon double bond (e.g., with the aldehyde group attaching to one of the carbons of the carbon-carbon double bond, and the hydrogen atom attaching to the other). In some instances, such as where the $H_2$ and CO partial pressures are high, a hydroxyl group may result as opposed to an aldehyde group. Hydroformylation generally occurs in the presence of a gas stream that comprises $H_2$ and CO, or in the presence of a gas from which one or both can be generated. For example, in some embodiments, syngas is used as the source of $H_2$ and CO for the hydroformylation reaction. Hydroformylation reactions are generally catalyzed, for example, by homogeneous catalysis. A typical hydroformylation reaction is shown below in Equation (D):

$$(R^a)(R^b)C{=}C(R^b)(R^d)+H_2+CO \leftrightarrows (R^a)(R^b)CH—C(CHO)(R^c)(R^d)+(R^a)(R^b)(CHO)C—CH(R^c)(R^d), \quad (D)$$

wherein $R^a$, $R^b$, $R^c$, and $R^d$ are hydrogen or organic groups, where at least one of $R^a$, $R^b$, $R^c$, and $R^d$ is not hydrogen. Depending on the identity of the olefin and/or the catalyst, among other factors, the hydroformylation can be selective to one of the two products over the other. Consider, for example, when $R^a$ is hydrogen, and $R^b$, $R^c$, and $R^d$ are organic groups, which is shown below in Equation (E):

$$(R^b)CH{=}C(R^c)(R^d)+H_2+CO \leftrightarrows (R^b)CH_2—C(CHO)(R^c)(R^d)\text{(branched and/or iso)}+(R^b)(CHO)CH—CH(R^c)(R^d)\text{(linear and/or normal)}, \quad (E)$$

wherein $R^b$, $R^c$, and $R^d$ are as defined above in Equation (D). The product obtained when the CHO adds to the more hydrogen-rich of the olefinic carbons is referred to as the "normal" or "linear" hydroformylation product, while the product obtained when the CHO adds to the less hydrogen-rich of the olefinic carbons is referred to as the "iso" hydroformylation product. In some embodiments, the hydroformylation reaction can be carried out so as to form a greater amount of the normal product than the iso product.

Any suitable process conditions and combination of catalysts can be used for the hydroformylation. The selection of suitable reaction conditions and catalyst can depend on a variety of factors, including, but not limited to, the scale of the reaction, the compositional makeup of the input stream, the desired compositional makeup of the output stream, any desired selectivity in the hydroformylation (e.g., where the input stream comprises polyunsaturated olefins), the stage of the process, cost of available catalysts, etc. Non-limiting examples of such processes include the BASF-oxo process, the Shell process, the Exxon process, the Union Carbide process, and the Rurhchemie/Rhone Poulenc process. Suitable catalysts include, but are not limited to, complexes of cobalt or rhodium. In certain embodiments, the hydroformylation catalyst is a rhodium complex.

In some embodiments, the input stream comprises one or more polyunsaturated alkenes, such as dienes or trienes. In some such embodiments, these trienes and dienes are non-conjugated dienes and trienes. In some embodiments, these dienes and trienes include one or more compounds with a terminal carbon-carbon double bond (i.e., a terminal alkene group). In any of these instances, it can be desirable to hydroformylate fewer than all of the carbon-carbon double bonds in the compound, e.g., only one of the two or more carbon-carbon double bonds, which is referred to herein as "selective hydroformylation." Such selective hydroformylation can be achieved, for example, by using reduces syngas pressures, e.g., pressures no more than 250 psi, or no more than 200 psi, or no more than 150 psi, or no more than 100 psi. The partial pressures of $H_2$ to CO can be varied relative to each other depending on a variety of factors, including, but not limited to, the nature of the reactants, the nature of the desired products, the catalyst system, etc. In some embodiments, the ratio of partial pressures of $H_2$ to CO is from 1:2 to 10:1.

Hydroformylation can be performed on any suitable olefin, including both olefinic hydrocarbons and olefinic esters. In some embodiments of the methods disclosed herein, the input to the hydroformylation is enriched in olefinic hydrocarbons relative to olefinic esters. For example, the weight-to-weight ratio of olefinic hydrocarbons to olefinic esters in the input stream is at least 2:1, or at least 3:1, or at least 4:1, or at least 5:1, or at least 7:1, or at least 10:1, or at least 15:1, or at least 20:1, or at least 35:1, or at least 50:1, or at least 100:1. This enrichment can be effected by any suitable means. For example, in some embodiments, the olefinic hydrocarbons are separated from the olefinic esters by a separation step, including, but not limited to, one or more of the separation methods described above. These olefinic hydrocarbons (i.e., alkenes) can comprise both monounsaturated alkenes and polyunsaturated alkenes. In some embodiments, however, the input stream can be enriched in polyunsaturated alkenes, e.g., because the polyunsaturated alkenes have been separated from the monounsaturated alkenes. Any suitable separation means can be used to separate polyunsaturated alkenes in a product stream from monounsaturated alkenes.

In embodiments where the input stream is enriched in olefinic hydrocarbons (or even polyunsaturated olefinic hydrocarbons), the composition of the input stream can vary depending on the various processing steps that have preceded the hydroformylation, as well as the identity of the natural oil feedstock or the unsaturated ester. For example, the refining processes can include any combination of metathesizing, transesterifying, separating, and/or hydrogenating, and can even include two or more steps of any of the foregoing. Non-limiting examples of potential refining processes are described in further detail in the following section.

In embodiments where a natural oil feedstock is the input, or where the unsaturated ester is derived from a natural oil feedstock, a variety of different olefinic hydrocarbons can be made in the course of the methods disclosed herein. Non-limiting examples of olefinic hydrocarbons that can be made from performing metathesis of a natural oil feedstock or of an unsaturated ester derived from a natural oil feedstock, include, but are not limited to the olefins shown in Table 1 on the following page. Table 1 also shows various aldehydes that could be synthesized by hydroformylating the various olefins. The left column provides a non-exhaustive list of olefinic hydrocarbons that may be generated in the course of metathesizing a natural oil, and the right-hand column provides a non-exhaustive representative list of formylated hydrocarbons that may be synthesized from each of the olefins by hydroformylation. In certain embodiments, such as when the syngas pressure is high, one of more of the formyl groups of the formylated hydrocarbons could be replaced by a —$CH_2OH$ group.

TABLE 1

| Olefinic Hydrocarbons | Formylated Hydrocarbons |
|---|---|
| 3-Hexene | 3-Formylhexane |
| 1-Heptene | Octanal; 2-Formylheptane |
| 1,4-Heptadiene | 1-Formyl-4-heptene; 2-Formyl-2-heptene |
| 1,4-Cyclohexadiene | 1-Formyl-3-cyclohexene; 1,4-Diformylcyclohexane |
| 1,4-Pentadiene | 1-Formyl-4-pentene; 2-Formyl-4-pentene |
| 3-Nonene | 3-Formylnonane; 4-Formylnonane |
| 1-Decene | Undecanal; 2-Formyldecane |
| 3-Decene | 3-Formyldecane; 4-Formyldecane |
| 1,4-Decadiene | 1-Formyl-4-decene; 2-Formyl-4-decene |
| 1,4,7-Decatriene | 1-Formyl-4,7-decadiene; 2-Formyl-4,7-decadiene |
| 3-Dodecene | 3-Formyldodecane; 4-Formyldodecane |
| 6-Dodecene | 6-Formyldodecane |
| 3,6-Dodecadiene | 3-Formyl-6-dodecene; 4-Formyl-6-dodecene |
| 3,6,9-Dodecatriene | 3-Formyl-6,9-dodecadiene; 4-Formyl-6,9-dodecadiene |
| 6-Tridecene | 6-Formyltridecane; 7-Formyltridecane |
| 1,4-Tridecadiene | 1-Formyl-4-tridecene; 2-Formyl-4-tridecene |
| 6-Pentadecene | 6-Formylpentadecane; 7-Formylpentadecane |
| 3,6-Pentadecadiene | 3-Formyl-6-pentadecene; 4-Formyl-6-pentadecene |
| 6,9-Pentadecadiene | 6-Formyl-9-pentadecene; 7-Formyl-9-pentadecene |
| 3,6,9-Pentadecatriene | 3-Formyl-6,9-pentadecadiene; 4-Formyl-6,9-pentadecadiene |
| 9-Octadecene | 9-Formyloctadecane |
| 6,9-Octadecadiene | 6-Formyl-9-octadecene; 7-Formyl-9-octadecene |

In embodiments where a natural oil feedstock is the input, or where the unsaturated ester is derived from a natural oil feedstock, a variety of different olefinic esters can be made in the course of the methods disclosed herein. Non-limiting examples of olefinic esters that can be made from performing metathesis of a natural oil feedstock or of an unsaturated ester derived from a natural oil feedstock, include, but are not limited to the olefins shown in Table 2, below. Table 2 also shows various formylated ester compounds that could be synthesized by hydroformylating the various esters. The left column provides a non-exhaustive list of olefinic methyl esters that may be generated in the course of metathesizing a natural oil, and the right-hand column provides a non-exhaustive representative list of formylated methyl esters that may be synthesized from each of the esters by hydroformylation. In certain embodiments, such as when the syngas pressure is high, one of more of the formyl groups of the formylated esters could be replaced by a —$CH_2OH$ group.

TABLE 2

| Olefinic Methyl Esters | Formylated Methyl Esters |
|---|---|
| 9-Decenoate | 9-Formyldecanoate; 10-Formyldecanoate |

TABLE 2-continued

| Olefinic Methyl Esters | Formylated Methyl Esters |
|---|---|
| 9-Dodecenoate | 9-Formyldodecanoate; 10-Formyldodecanoate |
| 11-Dodecenoate | 11-Formyldodecanoate; 12-Formyldodecanoate |
| 9,12-Tridecadienoate | 12-Formyl-9-tridecenoate; 13-Formyl-9-tridecenoate |
| 11-Tetradecenoate | 11-Formyltetradecanoate; 12-Formyltetradecanoate |
| 9-Pentadecenoate | 9-Pentadecanoate; 10-Pentadecanoate |
| 9,12-Pentadecadienoate | 12-Formyl-9-pentadecenoate; 13-Formyl-9-pentadecenoate |
| 9-Octadecendioate | 9-Formyloctadecanedioate |
| Oleate | 9-Formyloleate; 10-Formyloleate |
| Linoleate | 12-Formyllinoleate; 13-Formyllinoleate |
| Linolenate | 15-Formyllinolenate; 16-Formyllinolenate |
| 9,12-Heneicosadiendioate | 12-Formyl-9-heneicosendioate; 13-Formyl-9-heneicosendioate |
| 9,12-Heneicosadienoate | 12-Formyl-9-heneicosenoate; 13-Formyl-9-heneicosenoate |

Derivation from Renewable Sources

The olefins and/or olefinic ester compounds employed in any of the aspects or embodiments disclosed herein can, in certain embodiments, be derived from renewable sources, such as from various natural oils or their derivatives. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin (or short-chain olefin) is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the short-chain olefin is 1-butene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the unsaturated esters may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

For example, multiple metathesis can be employed to make the extended-chain branched-chain ester compounds disclosed herein. In some embodiments, cross-metathesis of an oleate can yield 1-decene, which can be self-metathesized to form 9-octadecene, which can react with via condensation with an acid to form a branched-chain ester. The ester portion of the branched ester can also be derived from a renewable source. For example, cross-metathesis of an oleate can also yield 9-decenoate, which can be hydrolyzed to 9-decenoic acid, which can be hydrogenated to form decanoic acid. Other branched-chain ester compounds can be derived from renewable sources by analogous means.

The conditions for such metathesis reactions, and the reactor design, and suitable catalysts are as described below with reference to the metathesis of the olefin esters. That discussion is incorporated by reference as though fully set forth herein.

In the embodiments above, the natural oil (e.g., as a glyceride) is metathesized, followed by transesterification. In some other embodiments, transesterification can precede metathesis, such that the fatty acid esters subjected to metathesis are fatty acid esters of monohydric alcohols, such as methanol, ethanol, or isopropanol.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

Separation

As noted above, in some embodiments of the methods disclosed herein, it may desirable to separate certain compounds (or classes of compounds) from others in a particular composition, e.g., the product composition from metathesizing a natural oil. For example, in some embodiments, the metathesis reaction forms a metathesis product comprising olefins (e.g., one or more alkenes) and esters (e.g., one or more metathesized unsaturated esters). In some such embodiments, the olefins can be separated from the esters in the metathesized product. In some other embodiments, the esters can be separated from the olefins in the metathesized product. In some embodiments, the separation precedes further potential treatment steps, such as partial hydrogenation and/or transesterification. In some other embodiments, however, the metathesized product is transesterified before separation of the olefins or esters from the other. In some embodiments, the metathesized product is partially hydrogenated before separation of the olefins or esters from the other. In some embodiments, the metathesized product is partially hydrogenated and transesterified (in either order) before separation of the olefins or esters from the other.

Any suitable separation method and separation apparatus can be used, depending on various factors, including, but not limited to, the identity of the species being separated, the complexity of the separation, the desired purity of the separated species, the scale of the refining process, and the point in the refining process into which the separation occurs.

In certain embodiments, where certain components of in the metathesized product are separated from other components, recycled streams from downstream separation units can be introduced to the metathesis reactor in addition to the natural oil or unsaturated ester, and, in some embodiments, the low-molecular-weight olefin and/or mid-weight olefin. For instance, in some embodiments, a $C_{2-6}$ recycle olefin stream or a $C_{3-4}$ bottoms stream from an overhead separation unit may be returned to the metathesis reactor. In some embodiments, a light weight olefin stream from an olefin separation unit can be returned to the metathesis reactor. In some other embodiments, the $C_{3-4}$ bottoms stream and the light weight olefin stream are combined together and returned to the metathesis reactor. In some other embodiments, a $C_{15+}$ bottoms stream from the olefin separation unit is returned to the metathesis reactor. In yet some other embodiments, one or more of the aforementioned recycle streams are returned to the metathesis reactor. In some other embodiments, one or more of the recycle streams may be selectively hydrogenated to increase the concentration of mono-olefins in the stream.

In some other embodiments, various ester streams downstream of the transesterification can be recycled and/or returned to the metathesis reactor. In certain embodiments, a glycerolysis reaction may be conducted on the recycled ester stream to prevent or limit the amount of free glycerol entering the metathesis reactor. In some embodiments, the recycled ester stream can undergo a purification to limit the amount of methanol being recycled to the metathesis reactor. In some embodiments, the recycled ester stream is combined with a low-molecular-weight olefin and/or mid-weight olefin prior to conducting the glycerolysis reaction and entering the metathesis reactor. In another embodiment, the recycled ester stream can be partially or selectively hydrogenated to increase the concentration of monounsaturated esters in the stream. In embodiments comprising gylcerolysis, the glycerolysis reaction can limit or prevent free fatty acid esters (e.g., free fatty acid methyl esters) from entering the metathesis reaction and subsequently exiting the metathesis reactor as free fatty acid esters that may boil at temperatures close to the boiling point of various high-valued olefin products. In such cases, these ester components can be separated with the olefins during the separation of the olefins and esters. In some instances, such ester components may be difficult to separate from the olefins by distillation.

The metathesis reaction in the metathesis reactor produces a metathesized product. In some embodiments, the metathesized product enters a flash vessel operated under temperature and pressure conditions, which causes $C_2$ or $C_{2-3}$ compounds to flash off and be removed overhead. The $C_2$ or $C_{2-3}$ light-end compounds ("light-ends") are comprised of a majority of hydrocarbon compounds having a carbon number of 2 or 3. In certain embodiments, the $C_2$ or $C_{2-3}$ light ends are then sent to an overhead separation unit, wherein the $C_2$ or $C_{2-3}$ compounds are further separated overhead from the heavier compounds that flashed off with the $C_{2-3}$ compounds. These heavier compounds are typically $C_{3-5}$ compounds, which are carried overhead with the $C_2$ or $C_{2-3}$ compounds. After separation in the overhead separation unit, the overhead $C_2$ or $C_{2-3}$ stream may then be used as a fuel source. These hydrocarbons have their own value outside the scope of a fuel composition, and may be used or separated at this stage for other valued compositions and applications. In certain embodiments, the bottoms stream from the overhead separation unit containing mostly $C_{3-5}$ compounds is returned as a recycle stream to the metathesis reactor. In the flash vessel, the metathesized product that does not flash overhead is sent downstream for separation in a separation unit, such as a distillation column.

In some embodiments, further separations is performed by fractional distillation. Such distillation can involve one or more distillation columns, depending on the nature of the separation. In some embodiments, the separation can be combined with chemical modification, where certain species in the composition to be separated are chemically altered to make it easier to distill the desired species from other species in the composition.

Further, in some embodiments, certain olefinic hydrocarbons formed by the metathesis of a natural oil feedstock (or of an unsaturated ester derived from a natural oil feedstock) can be separated from other olefinic hydrocarbons formed in the same way. For example, in some such embodiments, certain olefinic hydrocarbons (e.g., $C_{4-20}$ olefinic hydrocarbons, or $C_{5-20}$ olefinic hydrocarbons, or $C_{6-20}$ olefinic hydrocarbons), or can be separated from lighter-weight olefinic hydrocarbons ($C_{2-3}$ olefinic hydrocarbons, or $C_{2-4}$ olefinic hydrocarbons, or $C_{2-5}$ olefinic hydrocarbons). Such separations can occur using a single fractional distillation column, or using two or more columns.

It should further be noted that the degree of separation can vary depending on the purpose for which the separation is carried out. Thus, as used herein, the terms "separate" or "separation" does not imply 100% separation. For example, in some embodiments, less than 100% of the separated compounds (e.g., olefins that are separated from esters) are recovered from the original composition. In some embodiments, the separation provides at least 60% recovery, or at least 70% recovery, or at least 80% recovery, or at least 90% recovery, or at least 95% recovery, or at least 99% recovery of the separated species from the original composition. Nor do the terms "separate" or "separation" imply that the separated fraction is 100% pure. Some amount of impurity can therefore be present, for example, in amounts up to 30 weight percent, or 20 weight percent, or 10 weight percent, or 5 weight percent, or 3 weight percent, or 1 weight percent, based on the total weight of the separated fraction. For example, in a separating process where olefins are being separated from esters, the separated olefin can still contain some amount of esters in the separated olefin stream as an impurity. In some embodiments, the separated product stream contains no more than 20 wt % impurities, or no more than 15% impurities, or no more than 10 wt % impurities, or no more than 5 wt % impurities, or no more than 1 wt % impurities, based on the total weight of the separated product stream.

Transesterification

In certain embodiments, the methods disclosed herein can incorporate one or more transesterification steps. In general, transesterification refers to a reaction that includes the exchange of organic groups between an alcohol and an ester. A typical transesterification reaction is shown below in Equation (C):

$$R^a—C(=O)—O—R^b+R^c—OH \leftrightarrows R^a—C(=O)—O—R^c+R^b—OH, \quad (C)$$

wherein $R^a$, $R^b$, and $R^c$ are organic groups, where the reaction is generally carried out in the presence of a catalyst, such as an acidic or basic catalyst, e.g., an alkali metal alkoxide, such as sodium methoxide.

The methods disclosed herein can optionally employ transesterification in a variety of different ways. For example, in embodiments where metathesis is carried out on a natural oil feedstock, the natural oil feedstock can comprise a variety of mono- and/or poly-functional esters, such as trigylcerides of fatty acids and/or free fatty acid esters. The metathesis of the natural oil feedstock can form metathesized esters, such as metathesized trigylcerides of fatty acids and/or metathesized free fatty acid esters. In some instances, it can be desirable to convert these metathesized esters to other esters that may be more useful for further downstream processing.

In some other embodiments, the natural oil can be transesterified prior to metathesis. As noted above, the natural oil feedstock can comprise a variety of mono- and/or poly-functional esters, such as trigylcerides of fatty acids and/or free fatty acid esters. In some embodiments, the natural oil feedstock comprises one or more unsaturated triglycerides, such as triglycerides that comprise one or more esters of oleic acid, linoleic acid, linolenic acid, or combinations thereof. Such triglycerides can be transesterified by reacting them with an alcohol (e.g., a mono-functional alcohol, such as methanol, ethanol, propanol, isopropanol, butanol, isobutanol, and the like, including any combinations thereof) in the presence of a catalyst (e.g., an acid or base, as noted above). In embodiments where the natural oil comprises one or more unsaturated triglycerides, transesterification can be used to form certain unsaturated esters, e.g., of mono-functional alcohols. For example, in embodiments where the unsaturated triglycerides comprise one or more esters of oleic acid, linoleic acid, or linolenic acid, transesterification can be used to form mono-functional esters of oleic acid, linoleic acid, or linolenic acid, such as methyl or ethyl esters of oleic acid, linoleic acid, or linolenic acid. Such unsaturated esters can be used as inputs for other useful process steps, such as metathesis and/or hydrogenation.

Any suitable alcohol can be used as a reactant in the transesterification, the selection of the alcohol or mixtures of alcohols being dependent on certain factors, such as the desired properties of identity of the resulting esters. In some embodiments, the alcohol is a mono-functional alcohol, where the organic group on the alcohol can be any suitable organic group, such as a hydrocarbyl group, which can be optionally substituted. In some embodiments, the organic group is an alkyl or alkenyl group. In some embodiments, the organic group is an alkyl group, such as methyl, ethyl, propyl, isopropyl, butyl, isobutyl, sec-butyl, and the like. In some embodiments, the alcohol used in the transesterification is methanol, ethanol, or a mixture thereof. In some embodiments, the alcohol is methanol. In some other embodiments, the alcohol is a polyhydric alcohol, such as glycerol, resulting in a glycerolysis.

Any suitable catalyst can be used. In general, transesterification reactions employ a homogeneous catalyst, such as an acid or base. In some embodiments, the catalyst is an alkali metal alkoxide, such as sodium methoxide. The concentration of the catalyst generally ranges from 0.5 to 1.0 wt %, based on the relative weight of the catalyst to the weight of the ester to be transesterified. The transesterification can be carried out at any suitable temperature and pressure. In general, the reaction is carried out at a temperature ranging from 0° C. to 120° C., or from 10° C. to 100° C., or from 40° C. to 80° C., or from 60° C. to 70° C. Further, the reaction is generally carried out in the range of atmospheric pressure, e.g., ranging from 0.5 to 2 atm, or from 0.7 to 1.5 atm, or from 0.8 to 1.3 atm, or from 0.9 to 1.1 atm.

As noted above, transesterification can produce a wide array of transesterified products, which, in some embodiments, can include saturated and/or unsaturated monomer fatty acid methyl esters ("FAMEs"), glycerin, methanol, and/or free fatty acids. In certain embodiments, the transesterified products, or a fraction thereof, may comprise a source for biodiesel. In certain embodiments, the transesterified products comprise $C_{10-15}$ or $C_{11-14}$ esters. In certain embodiments, the transesterified products comprise 9DA esters, 9UDA esters, and/or 9DDA esters. Non-limiting examples of 9DA esters, 9UDA esters and 9DDA esters include methyl 9-decenoate ("9-DAME"), methyl 9-undecenoate ("9-UDAME"), and methyl 9-dodecenoate ("9-DDAME"), respectively. As a non-limiting example, in a transesterification reaction, a 9DA moiety of a metathesized glyceride is removed from the glycerol backbone to form a 9DA ester.

In certain embodiments, transesterification follows metathesis and the olefins are separated from the metathesized product, either before transesterification of after. In some such embodiments, a composition comprising various fatty acid esters and alcohols (e.g., glycerol) can be obtained. In such instances, the fatty acid esters can be separated from the alcohols by certain known procedures, such as liquid-liquid extraction. Once separated, such fatty acid esters can be used for various purposes, such as inputs for a metathesis reaction or as a fuel source (e.g., biodiesel). In some embodiments disclosed herein, the metathesis is carried out on one or more unsaturated esters. In some such embodiments, the unsaturated esters, or a fraction of the unsaturated esters, can be obtained in this way. The separated alcohol (e.g., glycerin) can be used for various processes.

In some embodiments, the transesterified products can be sent to a hydrogenation unit for hydrogenation (e.g., selective hydrogenation), where the degree of unsaturation in the collected esters is higher than desired. Further details on hydrogenation and selective hydrogenation are described below.

In some embodiments, the transesterified products can be further processed in a water-washing unit. In such embodiments, the transesterified products undergo a liquid-liquid extraction when washed with water. Excess alcohol, water, and glycerol are removed from the transesterified products. In some such embodiments, the water-washing step is followed by drying, wherein excess water is removed from the ester composition. Such washed and dried esters can function as specialty chemicals. In some embodiments, such specialty chemicals include, but are not limited to, 9DA, 9UDA, and/or 9DDA, alkali metal salts and alkaline earth metal salts of the preceding, individually or in combinations thereof.

In some embodiments, the monomer specialty chemical (e.g., 9DA) may be further processed in an oligomerization reaction to form a lactone, which may serve as a precursor to a surfactant.

In certain embodiments, the transesterifed products from the transesterification unit or specialty chemicals from the water-washing unit or drying unit are sent to an ester distillation column for further separation of various individual or groups of compounds. This separation may include, but is not limited to, the separation of 9DA esters, 9UDA esters, and/or 9DDA esters. In one embodiment, the 9DA ester may be distilled or individually separated from the remaining mixture of transesterified products or specialty chemicals. In certain process conditions, the 9DA ester may be the lightest component in the transesterified product or specialty chemical stream, and come out at the top of the ester distillation column. In some embodiments, the remaining mixture, or heavier components, of the transesterified products or specialty chemicals, may be separated off the bottom end of the column. In some embodiments, this bottoms stream may potentially be sold as biodiesel.

Esters obtained from these products may be subjected to various reactions to form other potentially useful chemicals or chemical compositions. For example, in some embodiments, fatty acid esters can be hydrolyzed to form acids or various acid salts. Or, in some embodiments, fatty acid esters can be reacted with each other to form dimers.

Or, in some embodiments, the fatty acid esters, if they contain carbon-carbon double bonds, can be metathesized in certain metathesis reactions, such as self-metathesis or cross-metathesis. Further, in embodiments, there the fatty acid esters contain one or more carbon-carbon double bonds, the unsaturated fatty acids can be isomerized to form an isomerized unsaturated ester, which can also be used as inputs to metathesis reactions. In embodiments, the methods disclosed herein comprise metathesizing an unsaturated ester. In some such embodiments, the unsaturated esters (or a portion thereof) used in such reactions can be obtained in one or more of these ways.

Hydrogenation

In certain embodiments, the methods disclosed herein can employ hydrogenation, wherein, for example, one or more carbon-carbon double bonds in an olefin are hydrogenated to remove the unsaturation. In some such embodiments, the natural oil feedstock or unsaturated ester can be partially hydrogenated in advance of the metathesis, e.g., so as to reduce the degree of unsaturation. In some other embodiments, hydrogenation can be carried out on one or more of the products of metathesis reaction. For example, in some embodiments, the olefins in the metathesis product can be partially hydrogenated. In some other embodiments, the esters in the metathesis product can be partially hydrogenated. In some embodiments, polyunsaturated olefins or esters can be separated from other olefins and esters, respectively, and the selective hydrogenation performed only on the polyunsaturated compounds.

Any suitable process conditions can be used for the hydrogenation or partial hydrogenation. Choice of such conditions can vary depending on a number of factors, including, but not limited to, the identity of the species to be hydrogenated (including their degree of unsaturation), the stage of the refining process, and the desired degree and/or selectivity of the hydrogenation (e.g., diene-selective partial hydrogenation). In some embodiments, the hydrogenation comprises reacting the compound(s) to be hydrogenated in the presence of a hydrogenation catalyst for, e.g., 30-180 minutes, or 30-120 minutes, at a temperature ranging from, e.g., 150° C. to 250° C., in an atmosphere where the partial pressure of $H_2$ ranges from 25 to 1000 psig, or from 50 to 500 psig. The hydrogenation catalyst can be provided in any suitable concentration, e.g., from 0.01 wt % to 1.0 wt %, relative to the total weight of the olefins to be hydrogenated (e.g., polyunsaturated olefins).

In some embodiments, the hydrogenation comprises a partial hydrogenation of a polyunsaturated olefin to a monounsaturated olefin. The conversion rate of polyunsaturated olefins to monounsaturated olefins can vary depending on the particular application. In some embodiments, the hydrogenation conversion rate is at least 50%, or at least 60%, or at least 75%, or at least 85%, or at least 90%, or at least 95%. In some embodiments, the partial hydrogenation can be selective to certain carbon-carbon double bonds in the olefin. In some embodiments, the hydrogenation is selective, meaning that at least one carbon-carbon double bond is preserved in the olefin following the partial hydrogenation. In some embodiments, the selectivity of the partial hydrogenation is at least 70%, or at least 80%, or at least 90%, or at least 95%, or at least 99%. In some embodiments, the feedstock is treated prior to the hydrogenating step under conditions sufficient to diminish catalyst poisons in the feedstock, as discussed above. Any suitable hydrogenation catalyst can be used in such embodiments. In some embodiments, the hydrogenation catalyst is nickel, copper, palladium, platinum, molybdenum, iron, ruthenium, osmium, rhodium, iridium, or any combinations thereof. In some embodiments, the hydrogenation catalyst has been recycled, e.g., has been recovered from another hydrogenation reaction and reused.

Suitable methods of carrying out hydrogenation, such as diene-selective hydrogenation, are described in U.S. Patent Application Publication No. 2013/0217906, which is incorporated herein by reference as though fully set forth herein.

Isomerization

In some embodiments, the unsaturated esters or olefins, e.g., produced by the metathesis of a natural oil, can be isomerized by containing the unsaturated compound with an isomerizing agent that leads to a shifting of the carbon-carbon double bond to another position in the carbon chain. Any suitable method for isomerizing olefinic compounds can be used. For example, in some embodiments, the methods can include isomerizing methods described in U.S. Patent Application Publication No. 2013/0204022, which is incorporated herein by reference as though fully set forth herein.

Derivatization of Formulated Hydrocarbons

In certain embodiments, the methods disclosed herein include further reacting the one or more formylated hydrocarbons and/or formylated ester compounds to form various specialty chemicals, such as carboxylic acids, esters, amines, and alcohols.

In at least some embodiments, the one or more formylated hydrocarbons and/or formylated ester compounds from a refining process are oxidized to form one or more carboxylated hydrocarbons and/or carboxylated ester compounds. In such embodiments, the formylated hydrocarbons and/or formylated ester compounds are reacted in the presence of a suitable oxidizing agent so as to convert the aldehyde group to a carboxylic acid group (or an esterified derivative thereof, e.g., methyl ester). Any suitable oxidizing agent or combination of oxidizing agents can be used. In some embodiments, the oxidizing agent is a gas, such as oxygen or air. In some other embodiments, the oxidizing agent is potassium permanganate, nitric acid, chromium (VI) oxide, chromic acid, or any combinations thereof. Any suitable conditions, e.g., temperature, pressure, etc., can be used. In some embodiments, the carboxylated hydrocarbons and/or carboxylated ester compounds can be further converted to an ester and/or diester, e.g., by oxidizing the aldehyde group in the presence of an alcohol, such as methanol. Or, in some other embodiments, the one or more carboxylated hydrocarbons can be reacted separately with an alcohol (e.g., methanol) to form an ester, such as a methyl ester. Or, in some other embodiments, the one or more carboxylated hydrocarbons and/or carboxylated ester compounds can be reacted separately with an amine (e.g., ammonia, methyl amine, or dimethyl amine) to form amides. Such reactions can be carried out on any of the formylated compounds recited in Table 1 and Table 2. The acids or esters formed by the process can be separated, if necessary, for use as a specialty chemical. In some embodiments, any unsaturated carboxylic acids can be separated from the saturated carboxylic acids, or vice versa, using techniques known to those of skill in the art.

In some embodiments, the one or more formylated hydrocarbons and/or formylated ester compounds from a refining process are reduced to form one or more hydroxylated hydrocarbons (including diols) and/or hydroxylated ester compounds. In such embodiments, the formylated hydrocarbons and/or formylated ester compounds are reacted in the presence of a suitable reducing agent so as to convert the aldehyde group to a primary alcohol. Any suitable reducing agent can be used. In some embodiments, the reducing agent is hydrogen gas. In some such embodiments, the reduction can occur in the same reactor as the hydroformylation, wherein the carbon-carbon double bond is hydroformylated followed immediately by the reduction of the formyl group to a primary alcohol. In some other such embodiments, the aldehyde can be isolated and reduced to the alcohol in a separate step. In embodiments where hydrogen is a reducing agent, such reactions can be done in the presence of a catalyst, such as metal, e.g., platinum, palladium, ruthenium, etc. In some other embodiments, the reducing agent is lithium aluminium hydride, diisobutylaluminium hydride, sodium borohydride, L-selectride, diborane, diazene, aluminum hydride, sodium cyanoborohydride, 9-BBN-pyridine, tributyltin hydride, or combinations thereof. Any suitable conditions, e.g., temperature, pressure, etc., can be used. Such reactions can be carried out on any of the formylated compounds recited in Table 1 and Table 2. The alcohols formed by the process can be separated, if necessary, for use as a specialty chemical. In some embodiments, any unsaturated alcohols can be separated from the saturated alcohols, or vice versa, using techniques known to those of skill in the art.

In some embodiments, the one or more formylated hydrocarbons and/or formylated ester compounds from a refining process are reduced to form one or more iminated hydrocarbons and/or iminated esters, or, in certain embodiments, are further reduced to form aminated hydrocarbons and/or aminated esters. In such embodiments, the formylated hydrocarbons and/or formylated esters are reacted in the presence of a suitable reducing agent and an amine so as to convert the aldehyde group to an amine, such as a primary amine. Any suitable reducing agent can be used. In some other embodiments, the reducing agent is lithium aluminium hydride, diisobutylaluminium hydride, sodium borohydride, L-selectride, diborane, diazene, aluminum hydride, sodium cyanoborohydride, 9-BBN-pyridine, tributyltin hydride, or combinations thereof. In some embodiments, the conditions may be adjusted to allow one to make the amine from the aldehyde in a single pot, e.g., with isolating the imine. Further, any suitable amines can be used, including ammonia, primary amines, and secondary amines. Any suitable conditions, e.g., temperature, pressure, etc., can be used. Such reactions car be carried out on any of the formylated compounds recited in Table 1 and Table 2. The imines and/or amines formed by the process can be separated, if necessary, for use as a specialty chemical. In some embodiments, any unsaturated imines or amines can be separated from the saturated imines or amines, or vice versa, using techniques known to those of skill in the art.

In some further embodiments, the one or more aminated hydrocarbons and/or aminated esters can be further reacted to form one or more hydrocarbons and/or esters having an isocyanate group. In such embodiments, the one or more aminated hydrocarbons is reacted with an electrophilic agent, such as phosgene, to form one or more hydrocarbons having an isocyanate group. Any suitable conditions, e.g., temperature, pressure, etc., can be used. Such reactions car be carried out starting with any of the formylated compounds recited in Table 1 and Table 2. The isocyanates formed by the process can be separated, if necessary, for use as a specialty chemical. In some embodiments, any unsaturated isocyanates can be separated from the saturated isocyanates, or vice versa, using techniques known to those of skill in the art.

In some embodiments, where the metathesized product includes two or more carbon-carbon double bonds, hydroformylation can be employed to form hydrocarbons and/or esters functionalized with two or more non-carbon functional groups. For example, in some embodiments, the metathesized product includes one or more diene hydrocarbons and/or triene hydrocarbons (which, in some embodiments, are separated from mono-ene in the metathesis product). Such dienes or trienes can be hydroformylated at two or more locations. For example, in some embodiments, a diene can be hydroformylated so as to formylate (or, in some circumstances, hydroxylate) both carbon-carbon double bonds in the diene. For example, 1,4-pentadiene, which can be made via the metathesis of a natural oil feedstock, can be hydroformylated at both olefinic bonds to form heptanedial, or, in certain embodiments, 1,7-heptanediol. In another example, 1,4-cyclohexadiene, which can be made via the metathesis of a natural oil feedstock, can be hydroformylated at both olefinic bonds to form 1,4-cyclohexanedial, 1,3-cyclohexanedial, or a mixture thereof. In some embodiments, such dials can be further reduced in the same pot to form 1,4-dimethanolcyclohexane, 1,3-dimethanolcyclohexane, or a mixture thereof. Any such dials, trials, diols, or triols can be further reacted to form functional groups according to the reactions described in the preceding section. These principles can be further extended to unsaturated esters and/or hydrocarbons having any number of carbon-carbon double bonds.

For example, in some embodiments, a diene or triene hydrocarbon is hydroformylated at two olefinic bonds to form a dial, which if further reacted, as described above, to form a diacid. In some embodiments, the diene is 1,4-pentadiene, and the resulting diacid is pimelic acid.

Any of the above reactions can also be combined with hydrogenation. For example, in some embodiments, an olefinic hydrocarbon and/or olefinic ester compound may have two or more carbon-carbon double bonds, where fewer than all of the carbon-carbon double bonds are hydroformylated and one or more non-hydroformylated carbon-carbon double bonds are hydrogenated.

The above methods may be suitable combined to make a wide variety of different compounds, including, but not limited to, 1,11-undecanedioic acid, 11-hydroxy-undecanoic acid, 1,11-undecanediol, 11-aminoundecanol, cyclic ethylene undecanedioate, 1,14-tetradecanedioic acid, 14-hydroxy-tetradecanoic acid, 14-amino-tetradecanoic acid, 1,14-tetradecanediol, 14-amino-tetradecanol, 1,14-diamino-tetradecane, 3-methyl-oxacycltetradecan-2-one, oxacyclopentadecan-2-one, 9-carboxyl-dodecanoic acid, 10-carboxyl-dodecanoic acid, 9-(hydroxymethyl)-dodecanoic acid, 10-(hydroxymethyl)-dodecanoic acid, 9-(aminomethyl)-dodecanoic acid, 10-(aminomethyl)-dodecanoic acid, 9-(hydroxymethyl)-dodecanol, 10-(hydroxymethyl)-dodecanol, 9-(hydroxymethyl)-dodecanamine, 10-(hydroxymethyl)-dodecanamine, 9-(aminomethyl)-dodecanol, 10-(aminomethyl)-dodecanol, 9-(aminomethyl)-dodecanamine, 10-(aminomethyl)-dodecanamine, and the like. In some embodiments, one can employ other common transformations of aldehydes, including but not limited to, Tollin's, aldol, and Tischenko transformations.

EXAMPLES

Example 1—Hydroformylation of Biorefinery Olefins and Unsaturated Esters

All olefin feedstock materials were pre-treated by heating to 200° C. for 2 hours to reduce peroxide value to less than 0.5 meq/kg. Methyl 9-decenoate was 98.8% pure. It contained 1.0% methyl 8-decenoate and 0.2% methyl decanoate. 9,12-Tridecadienoate was 95.8% pure. It contained 0.25% saturated C13 FAME and 0.62% of mono-unsaturated C13 FAME. The C10 olefin consisted mainly of 1-decene (91.8%), internal C10 olefins (2.5%). The balance consisted of other olefins and FAMES.

Hydroformylation experiments were conducted in a 3-ounce Fisher-Porter tube equipped with a 20 mm cross-shaped stir bar, a digital pressure gauge capable of measuring pressure to a tenth of a PSI, a sealable port for the introduction of liquid reagents, a vent line to de-pressure the reactor through the headspace, and a gas manifold capable of delivering nitrogen, hydrogen, or syngas at a pressure of at least 100 psig. Gas was delivered to the Fisher-Porter tube through a dip-tube. The Fischer-Porter tube was submerged in a silicone oil bath. Heating and stirring was provided by a Magnetic Stirrer/Hotplate.

Except where otherwise noted, manipulation of chemicals was performed with standard air-free lab techniques. The reactor was loaded, in a dry-box, with $R^h(acac)(CO)_2$ (ca 5 to 6 mg), triphenylphosphine, and olefinic substrate (ca 27 mmole), and undecane (ca 0.5 g as an internal standard). The sealed reactor was brought out of the dry box and then attached to the gas manifold. It was pressured to 95 psig with nitrogen followed by venting to 0 psig (2 times). Toluene was added through sealable port to bring total volume to 27 mL. The stir rate was set to 1500 rpm creating a deep vortex. The reactor was pressured to 95 psig and vented to 0 psig three times with nitrogen then 3 times with hydrogen. The reactor was then pressured to 95 psig with syngas, vented to 0 psig. Finally, the reactor was pressurized and heated to specified reaction conditions. Pressure was maintained by continuous syngas feed set at the specified pressure. The reaction mixture was analyzed by GC after the indicated time.

Table 3 shows the conditions for hydroformylation experiments performed on four different substrates, denominated as Examples 1a to 1c.

TABLE 3

| | Reactor Charge | | | Reaction Conditions | | |
|---|---|---|---|---|---|---|
| Example | Feedstock | Rh(CO)2acac | Triphenyl-phosphine | Temp (° C.) | Pressure (PSIG) | Time (min) |
| 1a | Methyl 9-decenoate (5.02 g) | 5.2 mg | 1.28 g | 80 | 95 | 135 |
| 1b | 9,12-Tridecadienoate (6.03 g) | 5.9 mg | 0.76 g | 80 | 80 | 100 |
| 1c | C10 olefin - mainly 1-decene (5.81 g) | 5.9 mg | 0.12 g | 90 | 110 | 120 |

Table 4 shows the results from the hydroformylation of the four substrate materials shown in Table 3. The "linear" addition of the formyl group refers to addition at the terminal carbon atom, while "branched" addition refers to addition of the formyl group at the non-terminal carbon.

TABLE 4

| | Crude Product Composition (percent) | | | | |
|---|---|---|---|---|---|
| Example | Unreacted olefin | Isomerized olefin | Hydroge-nated | Linear aldehyde | Branched aldehyde |
| 1a | 4.5 | 2.7 | 0.3 | 75.6 | 16.9 |
| 1b | 23.7 | 13.5 | 1.5 | 50.2 | 11.1 |
| 1c | 1.6 | 3.4 | trace | 66.9 | 22.6 |

The invention claimed is:

1. A method for refining a natural oil derivative, comprising:

providing a reactant composition comprising olefinic ester compounds, which are 9-dodecenoic acid esters;

reacting the olefinic ester compounds with $H_2$ and CO in the presence of a hydroformylation catalyst to form a product composition comprising (a) hydroformylation catalyst residues, and (b) formylated ester compounds or hydroxylated ester compounds; and separating at least a portion of the hydroformylation catalyst residues from other compounds from the product composition.

2. The method of claim 1, wherein the product composition is a nonpolar composition having a single phase.

3. The method of claim 1, wherein the product composition comprises a polar phase and a nonpolar phase.

4. The method of claim 3, wherein the nonpolar phase comprises at least a portion of the formylated ester compounds or hydroxylated ester compounds.

5. The method of claim 1, wherein the separating comprises carrying out a liquid-liquid extraction, wherein the extraction comprises removing a polar phase that comprises the hydroformylation catalyst resides from a nonpolar phase that comprises other compounds from the product composition.

6. The method of claim 1, wherein the product composition comprises one or more formylated ester compounds.

7. The method of claim 1, wherein the esters of 9-dodecenoic acid are derived from a process that comprises:

providing one or more low-molecular-weight olefins and a natural oil feedstock comprising unsaturated esters;

cross-metathesizing the low-molecular-weight olefins with the unsaturated esters to form a metathesized product comprising metathesized olefins and metathesized unsaturated esters;

optionally separating at least a portion of the metathesized unsaturated esters from other components of the metathesized product; and optionally transesterifying the metathesized unsatutared esters with a low-molecular-weight alcohol.

8. The method of claim 7, wherein the esters of 9-dodecenoic acid are 9-dodecenoic acid glycerides.

* * * * *